United States Patent [19]

Hseih

[11] Patent Number: 5,023,252

[45] Date of Patent: Jun. 11, 1991

[54] TRANSDERMAL AND TRANS-MEMBRANE DELIVERY OF DRUGS

[75] Inventor: Dean Hseih, Brandamore, Pa.

[73] Assignee: Conrex Pharmaceutical Corporation, Malvern, Pa.

[21] Appl. No.: 449,117

[22] Filed: Dec. 8, 1989

Related U.S. Application Data

[63] Continuation of Ser. No. 138,830, Dec. 28, 1987, abandoned, Continuation-in-part of Ser. No. 899,049, Aug. 21, 1986, abandoned, Continuation-in-part of Ser. No. 804,661, Dec. 4, 1985, abandoned.

[51] Int. Cl.$^5$ .............................................. A61K 31/55
[52] U.S. Cl. ................... 514/183; 514/431; 514/450
[58] Field of Search ............... 514/946, 947, 183, 431, 514/450, 210–212, 218, 222, 234, 236–238, 247, 346, 348, 352, 424, 426, 430–432, 445, 447, 449, 450, 451, 452, 454–461, 473, 508, 513, 515, 529, 533, 536, 638, 675, 676, 690, 599, 613

[56] References Cited

U.S. PATENT DOCUMENTS

| | | | |
|---|---|---|---|
| 3,474,176 | 10/1969 | Freeman et al. | |
| 3,921,636 | 11/1975 | Zaffaroni | 424/434 |
| 3,964,482 | 6/1976 | Gerstel et al. | 424/434 |
| 3,996,934 | 12/1976 | Zaffaroni | 424/434 |
| 4,405,616 | 9/1983 | Rajadhyaksha | 514/212 |
| 4,415,563 | 11/1983 | Rajadhyadsha | 514/946 |
| 4,557,934 | 12/1985 | Cooper . | |
| 4,590,170 | 5/1986 | Akiyoshi et al. | 436/533 |
| 4,710,497 | 12/1987 | Heller et al. | 514/947 |

FOREIGN PATENT DOCUMENTS

| | | | |
|---|---|---|---|
| 0129284 | 12/1988 | European Pat. Off. | 524/946 |
| 2142237A | 1/1985 | United Kingdom . | |
| PCT/US86/-02583 | 6/1987 | World Int. Prop. O. . | |

OTHER PUBLICATIONS

Jones, "Transdermal and Related Drug Delivery Systems", Noyes Data Corp. (U.S.A.), pp. 109–137, (1984).

*Primary Examiner*—Helen S. Sneed
*Assistant Examiner*—James Saba
*Attorney, Agent, or Firm*—Alexis Barron

[57] ABSTRACT

The rate of absorption of drugs across skin and other body membranes such as mucous membranes and the blood brain barrier is enhanced by adding to the drug composition a compound which enhances the rate. This compound may be macrocyclic ester, diester, amide, diamide, amidine, diamidine, thioester, dithioester, thioamide, ketone or lactone. The macrocyclic ketone contains at least 12 carbon atoms.

53 Claims, 20 Drawing Sheets

TRANSDERMAL AND TRANS-MEMBRANE DELIVERY OF DRUGS

This is a continuation of copending application Ser. No. 07/138,830 filed on Dec. 28, 1987 which is a continuation-in-part of patent application Ser. No. 899,049, filed Aug. 21, 1986, now abandoned, which is a continuation-in-part of patent application Ser. No. 804,661, filed Dec. 4, 1985, and now abandoned.

INVENTION

This invention relates to transdermal and transmembrane delivery of physiologically active agents such as drugs to humans and animals. It particularly relates to systems for delivering of drugs across skin, membranes of various body cavities such as occular, nasal, oral, buccal, anal, rectal, vaginal, and blood brain barrier and like membranes, and providing an enhanced rate of passage across such skin or membranes.

BACKGROUND OF THE INVENTION

Naturally, body membranes of all sorts represent protective barriers against foreign materials and infection. However, administration of drugs using transdermal and trans-membrane delivery systems does provide improved therapeutic advantages and better patient compliances which is well known and documented in both the patent and scientific literature. Examples of such systems are disclosed in U.S. Pat. Nos. 3,921,636; 3,964,482; 3,989,816; 3,996,934; 4,201,211; 4,291,014; 4,291,015; 4,292,203; 4,336,243; 4,346,709; 4,379,454; 4,409,206; 4,460,372; 4,486,193; and 4,490,322.

Administration using transdermal and trans-membrane drug delivery systems has certain advantages over the conventional methods of oral and systemic administration. These advantages include: (1) minimizing drug exposure by allowing a significant reduction in dosage; (2) providing long-term therapy in a single dose thereby increasing patient compliance; (3) avoiding the risks and inconveniences of intravenous or intramuscular therapy; (4) rendering possible the use of drugs with short biological half-lives; (5) allowing immediate termination of drug input by simply removing the material containing the drug; and (6) avoiding the possible inactivation of a drug when it first passes through the liver after oral administration.

Examples of drugs which have been administered transdermally include scopolamine, nitroglycerine, clonidine, estradiol, antibiotics (e.g., erythromycin, lincomycin, and the like), antifungal agents, and sunscreens. Many of these drugs, e.g., clonidine, scopolamine, and nitroglycerine are of such chemical structure that they can permeate the skin and other body membranes to provide sufficiently high therapeutic doses for most purposes. However, when higher therapeutic levels are required, or when the drug itself, e.g., estradiol diacetate, does not permeate or cannot sufficiently permeate the skin to provide the desired level of drug concentration, it becomes necessary to use adjuvants which enhance the rate of penetration of the drug. Generally, for transdermal formulation of most drug entities adjuvants are required.

TRANSMEMBRANE DELIVERY OF DRUGS

Besides skin, mucous membranes cover the surface area of various body cavities such as nasal, oral, buccal, anal, rectal, and vaginal, which protect the body from the invasion of foreign materials. These membranes represent alternative routes of drug administration; in particular, for such drugs as peptides and proteins or other macromolecules (generally speaking, molecular weight larger than 1,000 daltons produced by genetic engineering or biotechnology). An example of transnasal delivery of insulin, molecular weight of 6,500 daltons, enhanced by surfactant in rats was reported by Hirai, Yashiki and Mima in the International Journal of Pharmaceutics, Vol. 9, pages 165–172, 1981 and International Journal of Pharmaceutics, Vol 9, pages 173–184, 1981. Further studies in human subjects (using insulinbile salt aerosol) were reported by Moses, Gordon, Carey, and Flier in Diabetes Vol. 3 pages 1040–1047, 1983. Nasal spray of insulin could possibly eliminate the need of subcutaneous insulin injection by diabetics and better patient compliances could possibly be achieved.

The uses of proteins, peptides, enzymes, nucleic acids, lipids, and complexes of thereof, as therapeutic agents have been documented. Oral administration is not suitable in most cases, as such drugs are destroyed in the digestive tract. Subdermal injections and implantation have inherent disadvantages, such as discomfort of administration, the necessity for administration by trained personnel, and problems with patient compliance. Transdermal administration has technical difficulties which was reviewed by Dean Hsieh in the chapter on Devices for Macro-molecules, pages 171–193, Transdermal Delivery of Drugs, Volume I, edited by Agis F. Kydonieus and Bret Berner, published by CRC Press. Therefore, with suitable penetration enhancers, transmembrane delivery of such macromolecules is an alternative route of choice for drug administration.

DELIVERY OF DRUGS THROUGH BLOOD-BRAIN BARRIER

The brain is surrounded by an endothelial capillary wall commonly known as the blood-brain barrier. This barrier is effective in protecting the brain from potentially harmful chemicals, but renders the administration of potentially beneficial drugs to the afflicted brain difficult, if not impossible, when the brain suffers from infection, tumor, or disfunction. Bodor and Farag reported a chemical redox drug delivery system to transmit drugs through blood-brain barrier. (See Bodor, H. and Farag, H. H., "Improved Delivery through Biological Membranes XIV: Brain-specific, Sustained Delivery of Testosterone Using a Redox Chemical Delivery System", in the Journal of Pharmaceutical Science, Vol. 73 (3), pages 385–388, 1984.) Drugs are bonded to a quarternary salt which is chemically reduced to a lipoidal dihydropyridine carrier. Upon administration, the compound is distributed throughout the body. The lipid-water partition ratio of the carrier allows it to deliver the drug to the brain. The compound is oxidized in vivo and reverts to its original form. The ionic, hydrophilic salt is quickly eliminated from the body, except that the blood-brain barrier (which works both ways) prevents its elimination from the brain. Enzymes remove the drug from the carrier, providing sustained release of drugs to the brain. No permeation enhancers were used in Bodor's work.

Compounds which have been used as adjuvants include dimethyl sulfoxide and homologs thereof, 1-alkylazacycloheptan-2-ones (azone), N,N-dimethyl-m-toluidine, long chain aliphatic alkanes, alcohols, carboxylic acids and esters and substituted (e.g., halo) derivatives thereof, cyclohexylalkanols, phenylalkanols, mixtures of siloxanes with either amides or urea derivatives, $C_{3-4}$ diols and ethers and esters thereof, mixtures of $C_{3-4}$ diols with surfactants, eucalyptol, urea, a mixture of 2-pyrrolidone and dimethyl formamide, 1,3-dimethyl-2-imidazolidinone, dicyclohexylmethylamine oxide, a mixture of hexane and ethylene glycol monomethyl ether, a mixture of ricinoleyl alcohol and an ethoxylated partial glycerine of a $C_{6-12}$ saturated fatty acid, N-substituted-diisopropylamines, and compounds of the formula $$R^1OCH_2-CH-CH_2O_2C\underset{\underset{O}{\overset{\|}{\underset{|}{HN}}}}{\phantom{XXXX}}$$

wherein $R^1$ and $R^2$ are hydrogen, $C_{1-25}$ alkyl, $C_{2-25}$ alkenyl, $C_{1-24}$ alkyl carbonyl, or $C_{2-24}$ alkenyl carbonyl.

While all of the above-listed adjuvants do serve to enhance the transdermal absorption of drugs, they possess certain drawbacks in that (i) some are regarded as toxic (e.g., dimethyl sulfoxide); (ii) some irritate the skin (e.g., surfactants); (iii) some on prolonged use have a thinning effect on the skin (e.g., oleic acid); and (iv) some change the intactness of the skin structure, resulting in a change in the diffusability of the drug (e.g., azone).

U.S. Pat. Nos. 3,921,636; 3,964,482 and 3,996,934 mention that cyclic ketones containing from 4 to 10 carbon atoms serve to enhance the transdermal absorption of drugs; however, no specific showing of such enhancement, or for that matter any transdermal absorption in the presence of such ketones, is shown.

Furthermore, my studies have demonstrated that there is little or no enhancement using cyclic ketones containing from 9 to 11 carbon atoms.

DESCRIPTION OF THE INVENTION

It is, accordingly, an object of this invention to provide a method for enhancing the rate of passage of drugs across skin, membranes of various body cavities, blood-brain barrier and like membranes.

It is another object of this invention to provide drug containing compositions which have an enhanced rate of passage across skin, membranes of various body cavities, blood-brain barrier and like membranes.

It is a further object of the invention to provide adjuvants or permeation enhancers which when added to drug compositions enhance the rate passage of the drug therein across skin, membranes of various body cavities, blood-brain barrier and like membranes.

It is still another object of this invention to provide adjuvants or permeation enhancers which are non-toxic and do not exert any physiological effects in the body other than enhancing the rate of passage of drugs across skin, membranes of various body cavities, blood-brain barrier and like membranes.

It is still another object of this invention to provide adjuvants or permeation enhancers which have a minimal effect on the structure of the skin, membranes of various body cavities, blood-brain barrier and like membranes.

It is a further another object of this invention to provide adjuvants or permeation enhancers which are compatible with drugs, pharmaceutical vehicles, and polymers.

Other objects will appear from the description which follows:

In accordance with this invention it has been found that the addition to a composition containing an effective amount of a drug and a compound of the structure;

$$\underset{(CR_3R_4)_m}{\overset{(X)_q}{\diagdown}}\overset{\overset{Y}{\|}}{\underset{\underset{(CR_5=CR_6)_p}{\diagup}}{C}}\underset{(A)_r}{\overset{(CR_1R_2)_n}{\diagup}}$$

wherein X and Y are oxygen, sulfur or an imino group of the structure $$-\underset{R}{\overset{|}{N}}-$$

or $=N-R$ with the proviso that when Y is the imino group, X is an imino group, and when Y is sulfur, X is sulfur or an imino group, A is a group having the structure $$-\overset{\overset{Y}{\|}}{C}-X$$

wherein X and Y are defined above, m and n are integers having a value from 1 to 20 and the sum of m+n is not greater than 25, p is an integer having a value of 0 or 1, q is an integer having a value of 0 or 1, r is an integer having a value of 0 or 1, and each of R, $R_1$, $R_2$, $R_3$, $R_4$, $R_5$ and $R_6$ is independently hydrogen or an alkyl group having from 1 to 6 carbon atoms which may be straight chained or branched provided that only one of $R_1$ to $R_6$ can be an alkyl group, with the proviso that when p, q and r have a value of 0 and Y is oxygen, m+n is at least 11, and with the further proviso that when X is an imino group, q is equal to 1, Y is oxygen, and p and r mare O, then m+n is at least 11, will enhance the rate of the passage of the drug across body membranes. Hereinafter these compounds are referred to as enhancers.

When R, $R_1$, $R_2$, $R_3$, $R_4$, $R_5$ or $R_6$ is alkyl it may be methyl, ethyl, propyl, isopropyl, butyl, isobutyl, sec-butyl, amyl, hexyl, and the like.

DETAILED DESCRIPTION OF THE INVENTION

Figure 1:
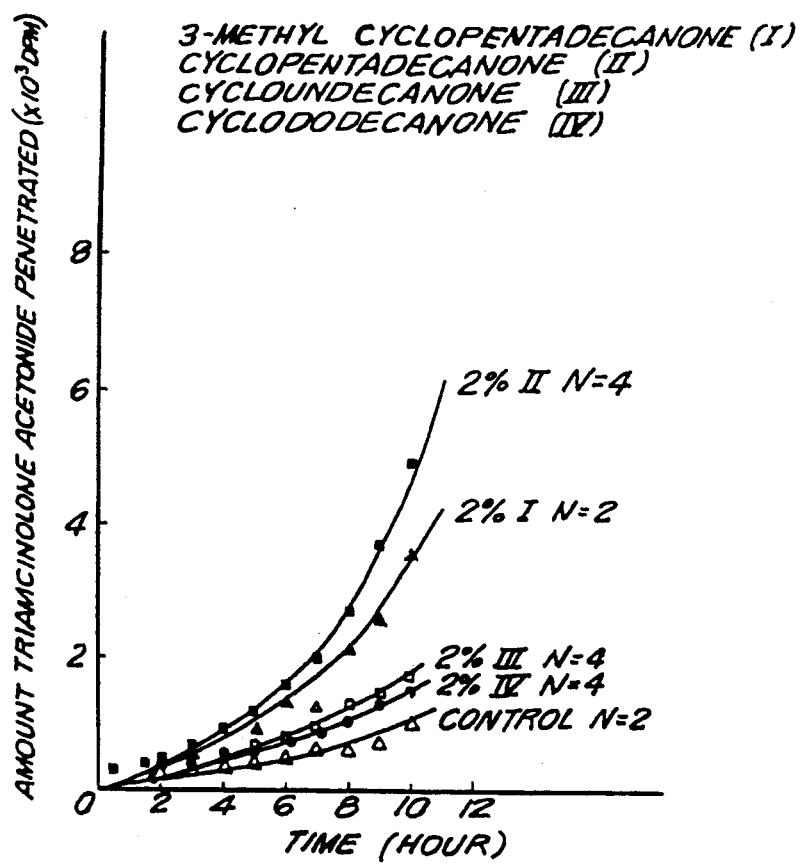
FIGS. 1 and 2, 4 to 6 inclusive 9 and 10, and 12 to 19 inclusive are graphs illustrating penetration profiles of compositions within the scope of the present invention and also control and comparative compositions.

In practicing this invention the enhancer is dissolved, dispersed, suspended, or solubilized in suitable solvent(s) such as alcohols, oils, glycerol, ethylene glycol, propylene glycol, hexane, acetone, freon, water, other polar or non-polar solvents, or their mixture thereof, which is then added to a composition comprising an effective amount of the desired drug admixed with a pharmaceutical carrier in an amount so that the concentration of the enhancer in the composition comprising the drug, pharmaceutical carrier and enhancer solution will be from about 0.1% to about 50% by weight. Preferably, the concentration of the enhancer will be from about 0.1% to about 30% by weight. In some cases, when the enhancers are in the liquid form a "neat" solution of enhancer can be directly incorporated in the drug, pharmaceutical carrier, and enhancer mixture, in which the concentration of enhancer ranges from 0.1% to about 30% by weight.

Pharmaceutical carriers include suitable non-toxic vehicles in which the drug is dissolved, dispersed, impregnated, or suspended, such as solvents, fatty materials, celluloses and their derivatives, proteins and their derivatives, collagens, gelatine, polymers, adhesives, sponges, fabrics, and the like and adjuvants which are added to provide better solubility or dispersion of the drug in the vehicle. Such adjuvants may include non-toxic surfactants, solubilizers, emulsifiers, chelating agents, binding materials, lubricants softening agents, and the like.

Preferably, the compounds of this invention are the cyclic lactones (the compounds wherein both X and Y are oxygen, (q is 1 and r is 0), the cyclic diesters (the compounds wherein both X and Y are oxygen, and both q and r are 1), and the cyclic ketones (the compounds wherein both q and r are 0 and Y is oxygen). In the cyclic diesters m+n is preferably at least 3. In the cyclic ketones m+n is preferably from 11 to 15 and p is preferably 0.

The drug composition, which may be administered topically, nasally, buccally, aurally, rectally, ocularly, orally, vaginally, or through the navel, may be in the form of solutions, creams, sprays, lotions, aerosols, suppositories or jellies; or incorporated in patches, films, tapes or bandages.

The invention will become clearer from the examples which follow taken in conjunction with the drawings which are described below. These examples and drawings illustrate preferred embodiments of the invention and are not to be regarded as limiting.

The evaluations of the composition of this invention in enhancing the rate of permeation of the drug were performed at various sites of the body. These sites included skin, mucous membranes of various body cavities, and blood-brain barrier.

The evaluation of the compositions of this invention in enhancing the rate of penetration of the drug through the skin was carried out in vitro using skin preparations obtained from homozygous Hr/Hr hairless mice (HRS/J) strain following the procedures described by Chow, Kaka and Wang in the J. Pharmaceut. Sci. 73 (12) 1794–1799 (1984) for the preparation, penetration study and data analysis.

Animals between 2 to 4 months of age were selected. In all selected animals the skins were grossly normal and free of bites, scratches or bruises. The mice were killed by $CO_2$ inhalation, and the skin was removed. The full-thickness skin was used in the penetration studies.

The skin preparation was mounted between the donor and receptor chambers of a Franz diffusion cell. The stratum corneum (SC) was exposed to the ambient condition and the dermal side was oriented toward a pH 7.4 saline-phosphate buffer, simulating the physiological pH of 7.3–7.4 of the dermal side, in the receptor chamber.

The solution of the receptor chamber was equilibrated by circulating water at 32° C. through a jacket surrounding the chamber, which temperature was chosen to reflect the temperature of the SC, prior to the applications of the test sample. Mixing of the solution in the receptor chamber was accomplished by magnetic stirring.

A known amount of a radioisotope-labeled drug, diluted with non-radioactive (cold) drug, with or without the adjuvant, was applied so as to spread across the SC surface of the mounted skin. Aliquots of the saline-phosphate buffer containing any radioisotope labeled drug which had penetrated through the skin into the receptor chamber were withdrawn from the side arm of the receptor chamber, and a volume of fresh saline-phosphate buffer equal to the volume of the withdrawn aliquot was added to the receptor chamber. Aliquots were withdrawn every thirty minutes during the first 2 hours and every hour during the next 10 hours, the total time of the study thus lasting up to 12 hours. The amount of the drug which had passed through the skin was measured by liquid scintillation counting of the withdrawn aliquot in Aquasol-2.

The drawings illustrate the penetration profiles of the drugs. These profiles were constructed by plotting the amount of the drug which had penetrated the skin versus time. Profiles for control samples (no adjuvant added) and for tested samples (containing an adjuvant) were plotted in the same figure for purposes of comparison.

The permeability parameters which are shown in the tables were calculated in accordance with the method of Chow, Kaka and Wang as described on page 1795 of their paper.

EXAMPLE 1

To a propylene glycol solution containing $4.74 \times 10^{-2}$ mg/ml of tritiated triaminolone acetonide 2% w/v of the adjuvant was added. The adjuvants tested were 3-methylcyclopentadecanone (I), cyclopentadecanone (II), cycloundecanone (III), and cyclododecanone (IV). Each of these cyclic ketones is commercially available. The preparations were tested according to the method described above, and the penetration profile of $H^3$ - triamcinolone acetonide as enhanced by each of these adjuvants is shown in FIG. 1, where each curve represents and average of the number of tests, N, carried with each adjuvant.

Based upon the data presented in FIG. 1, the total amount of tritiated triamcinolone acetonide and the rates of penetration (flux) calculated from the linear portion of the curve are shown in Table 1.

TABLE 1

| Adjuvant | Flux $\times 10^3$ dpm/ cm$^2$/hr | Ratio % | Total Amount* dpm ($\times 10^3$) | Ratio % |
|---|---|---|---|---|
| Control | 0.16 | 100 | 1 | 100 |
| I | 0.70 | 437 | 3.5 | 350 |
| II | 1.07 | 669 | 4.8 | 480 |
| III | 0.25 | 156 | 1.5 | 150 |

TABLE 1-continued

| Adjuvant | Flux × 10³ dpm/cm²/hr | Ratio % | Total Amount* dpm (× 10³) | Ratio % |
|---|---|---|---|---|
| IV | 0.25 | 156 | 1.7 | 170 |

*Total amount of triamincinolone acetonide which penetrated at the end of 10 hours.

EXAMPLE 2

Nasal absorption of insulin in dogs

The object of this study was to demonstrate that nasal absorption of therapeutic proteins, peptides, carbohydrates, nucleic acids, lipoproteins, mucoproteins, lipoproteins, and other macromolecules in living animals and humans can be achieved with the addition of skin enhancers such as cyclopentadecanolide.

Beagle dogs weighing 10 to 12 kg were used in this study. The formulation of the nasal spray was composed of Freon, insulin, and cyclopentadecanolide packaged in a metered nasal spray device which is commercially available. Before applying nasal spray in dogs, the dogs were anaesthesized using Nembutal (or pentabarbitol) at the dose of 40–50 mg/kg. Fifteen minutes before application, blood samples were obtained. The nasal spray of insulin was then applied with the aid of applicator. Blood samples were again obtained at 0, 10, 20, 30, 45, 50, 90, 120 and 180 minutes. Both blood glucose determined by YSI glucose analyzer and serum insulin levels determined by radioimmunoassay were tested. Both methods were commonly practiced in the laboratory.

Table 2 shows the blood glucose and serum insulin levels of dogs receiving insulin nasal spray containing cyclopentadecanolide. Obviously, when nasal spray of insulin with cyclopentadecanolide was applied (sprayed) in the nasal cavity of dogs, serum insulin levels abruptly increased to 71.2 uU/ml in 10 minutes and maintained the level for about 30 minutes, then gradually decreased and levelled off in 3 hours. On the other hand, blood glucose levels decreased from 83.6 mg/dl at 0 minute to 51.5 mg/dl at 30 minutes as serum insulin levels increased from 2.7 uU/ml at 0 minute to 67.1 uU/ml at 30 minutes. Then, the blood glucose levels maintained almost constant for about 80 minutes. Finally, when serum insulin was depleting at 120 minutes to 7.9 uU/ml at 180 minutes, blood glucose levels rose from 45.8 mg/dl to 72.7 mg/dl within the same time span.

Figure 2:
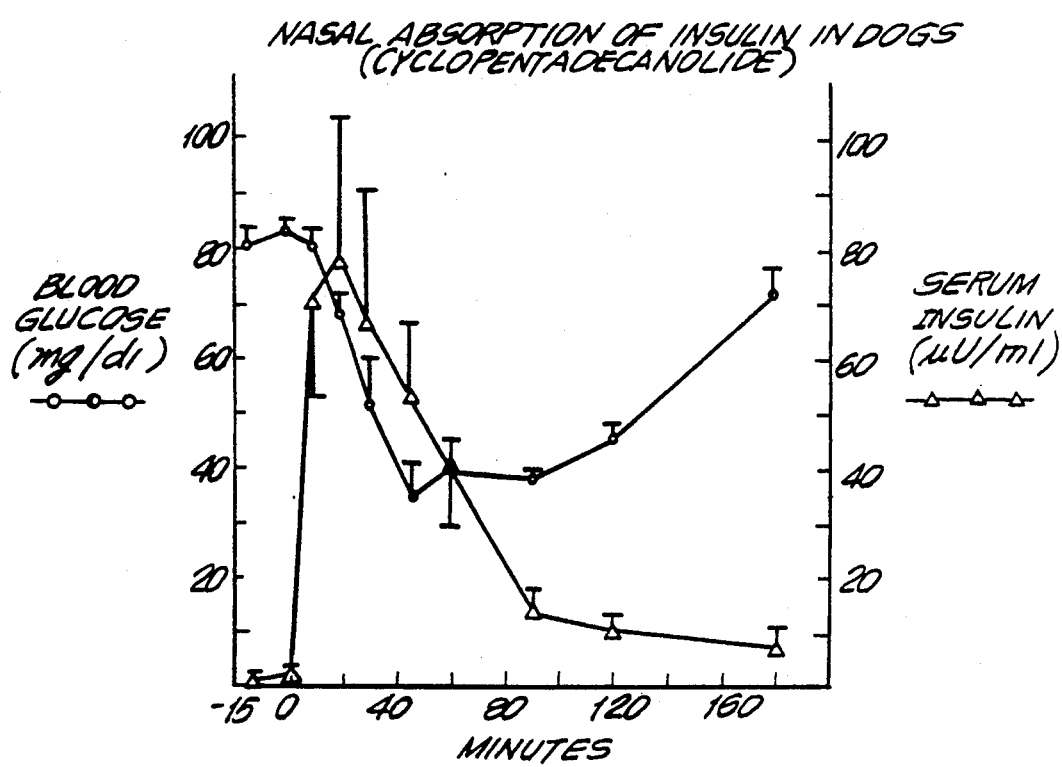

FIG. 2 shows the time course of both blood glucose and serum insulin levels in dogs before and after receiving nasal spray of insulin containing cyclopentadecanolide. These patterns were similar to those receiving insulin subcutaneously.

TABLE 2

Nasal Absorption of Insulin in Dogs with Cyclopentadecanolide

| Time (minutes) | Blood Glucose (mg/dl) | Serum Insulin (uU/ml) |
|---|---|---|
| −15 | 81.0 ± 3.2 | 1.7 ± 0.6 |
| 0 | 83.6 ± 1.6 | 2.7 ± 1.3 |
| 10 | 80.7 ± 2.7 | 71.2 ± 28.3 |
| 20 | 68.4 ± 9.1 | 78.6 ± 26.6 |
| 30 | 51.5 ± 9.5 | 67.1 ± 23.9 |
| 45 | 35.2 ± 6.6 | 53.3 ± 13.6 |
| 60 | 40.1 ± 5.3 | 40.7 ± 10.9 |
| 90 | 38.7 ± 0.4 | 14.2 ± 3.9 |
| 120 | 45.8 ± 3.0 | 10.8 ± 2.7 |
| 180 | 72.7 ± 8.3 | 7.9 ± 2.8 |

1. Three dogs were used in the study
2. Data were expressed as mean ± S.E.M.
3. The dose of insulin used in each dog was 1 U/kg body weight
4. The concentration of cyclopentadecanolide in Freon solution was 1%

Control experiments included the following:
(1) Placebo without insulin but containing skin enhancer, (2) Phosphate buffer solution, and (3) Insulin itself. When these control formulations were sprayed in the nasal cavity in dogs, no changes in both blood glucose level and serum insulin were found.

Example 2 illustrates the use of macrocyclic compounds in the nasal spray of insulin formulations for diabetes treatment. The practice of this invention as a spray is not limited to insulin alone, but is suitable for many therapeutic proteins and peptides. To name a few, interferon for common colds, cancer, and viral infection, lymphokines for cancer and immunity disease, growth hormones for dwarfism, luteinizing hormone releasing hormones (LHRH) analogs for birth control, enkaphaline for pain relief, and so on.

EXAMPLE 3

Nasal Insulin Spray for the Treatment of Diabetics

The objective of this study is to evaluate the efficacy of a nasal insulin spray containing macrocyclic compounds as permeation enhancers for diabetic treatment. The methodology of this study follows the methods published by two different groups of scientists. One was by Alan C. Moses, Gilad S. Gordon, Martin C. Carey, and Jeffrey S. Flier in Diabetes Vol. 32, p. 1040–1047, 1983, Insulin Administered Intranasally as an Insulin-Bile Salt Aerosol. The other was by Antonio E. Pontiroli, Miriam Alberetto, Antonio Secci, Giorgio Dossi, Isabella Bosi, and Guido Pozza, in British Medical Journal Vol 284, p. 303–306, 1982. Insulin given Intranasally Induced Hypoglycemia in Normal and Diabetic Subjects.

The enhancer used in this study is 1% cyclopentadecanolide and insulin used is U-200 porcine insulin. The tested subjects receive 4 sprays of enhancer solution (two sprays each nostril), then 2 sprays of U-200 (1 spray each nostril) or equivalent to 40 U per 60 kilograms. Before spraying, the subjects would fast for two hours. The subjects were asked to take a deep breath when nasal insulin spray was administered.

Blood samples were drawn 20 minutes before insulin administration. After spraying, blood samples were drawn every 30 minutes. Blood glucose levels were determined using radioimmuniassay.

Four subjects who have hyperglycemia history were selected to receive nasal insulin sprays. Two other subjects as a control group receiving either enhancer or insulin only.

The results obtained from four Type II diabetics are shown in Table 3. They clearly indicated that blood glucose levels can be decreased by receiving nasal insulin spray. In other words, insulin can be absorbed through nasal membrane when cyclopentadecanolide is incorporated into the formulation. This was further confirmed by the determination of serum insulin levels form the same blood samples. For the one who received enhancer spray only, the blood glucose levels did not decrease. Neither did it for the one who received insulin solution without enhancer.

TABLE 3

Blood glucose measurement of diabetics receiving nasal insulin spray.

| Time | Subject 1 | Subject 2 | Subject 3 | Subject 4 |
|---|---|---|---|---|
| −20 min. | <400 mg/dl | 276 mg/dl | 384 mg/dl | 308 mg/dl |
| 30 min | 399 | 246 | 334 | 277 |
| 60 min | 388 | 209 | 325 | 274 |
| 90 min | 342 | — | — | 266 |
| 120 min. | 339 | — | 279 | 244 |

1. Insulin solution is U-200 porcine insulin.
2. Permeation enhancer used is 1% cyclopentadecanolide in Freon.
3. Four subjects were Type II diabetics.
4. "−20 min" indicates that blood samples were taken 20 minutes before nasal spray.

EXAMPLE 4

Vaginal Sponge for Estrus Synchronization in Sheep. The objective of this study was to demonstrate the vaginal absorption of therapeutic agents can be achieved to desirable therapeutic levels by the addition of permeation enhancers such as cyclopentadecanolide. Polymer sponges made of polyurethane or the like were impregnated with 80% fluorogestorone acetate and 20% cyclopentadecanolide. The sponge was inserted into the vagina of ewes for up to 12 days. Blood samples were drawn and the levels of fluorogestorone acetate were determined by radioimmunoassay. Table 4 shows the blood levels of fluorogestorone acetate in ewes during the time course of treatment. The later phase of treatment is the decisive indicator for estrus synchronization in ewes. The results clearly indicated that at the alter phase of treatment (i.e., days 6, 9, and 12), the blood levels in those ewes receiving sponges containing permeation enhancers such as cyclopentadecanolide are higher than those without permeation enhancers.

TABLE 4

Blood levels of Fluorogestorone Acetate in Ewes

| Treatment and Animal No. | | 0 | 3 | Day of Treatment 6 | 9 | 12 | 13 |
|---|---|---|---|---|---|---|---|
| | | | | (Nanogram/ml) | | | |
| -ve Control | 1 | 3.61 | 0.19 | 0.47 | 0.22 | 0.20 | 0.34 |
| | 2 | 6.82 | 0.48 | 0.39 | 0.25 | 0.19 | 0.23 |
| | 3 | 0.69 | 0.36 | 0.36 | 0.07 | 0.09 | 0.32 |
| | X̄ | 3.70 | 0.34 | 0.41 | 0.18 | 0.16 | 0.30 |
| | SED | 1.77 | 0.08 | 0.03 | 0.05 | 0.03 | 0.03 |
| Sponge I (No Enhancer) | 4 | 0.56 | 2.61 | 1.42 | 2.05 | 1.11 | 0.39 |
| | 5 | 3.15 | 3.23 | 2.26 | 1.49 | 1.56 | 0.19 |
| | 6 | 5.51 | 3.26 | 3.61 | 2.53 | 2.41 | 0.43 |
| | 7 | 0.80 | 2.06 | 1.39 | 2.05 | 1.47 | 0.22 |
| | X̄ | 2.51 | 2.79 | 2.17 | 2.03 | 1.64 | 0.31 |
| | SED | 1.16 | 0.28 | 0.52 | 0.21 | 0.28 | 0.06 |
| Sponge II (With Enhancer) | 8 | 2.62 | 2.12 | 2.06 | 3.61 | 2.51 | 0.34 |
| | 9 | 0.87 | 4.27 | 2.53 | 2.31 | 2.13 | 0.41 |
| | 10 | 0.82 | 3.33 | 2.18 | 2.39 | 2.04 | 0.59 |
| | 11 | 1.06 | 2.02 | 2.22 | 2.81 | 2.24 | 0.63 |
| | X̄ | 1.34 | 2.94 | 2.56 | 2.78 | 2.23 | 0.49 |
| | SED | 0.43 | 0.54 | 0.10 | 0.30 | 0.10 | 0.07 |

Blood-Brain Barrier and Central Nervous System

The blood-brain barrier (BBB) is comprised of brain microvessel endothelial cells characterized by tight intercellular junctions, minimal pinocytic activity, and the absence of fenestra. These characteristics endow microvellel endothelial cells with ability to restrict passage of most small polar bloodborne molecules (e.g. neurotransmitter catecholamines, small peptides and macromolecules, e.g. proteins) from the cerebrovascular circulation to the brain. On the other hand, within the cerebrovasculature, the blood-brain barrier is a dynamic regulatory interface that poses a formidable barrier to delivery of pharmacological modalities to the central nervous system.

EXAMPLE 5

Figure 3A:
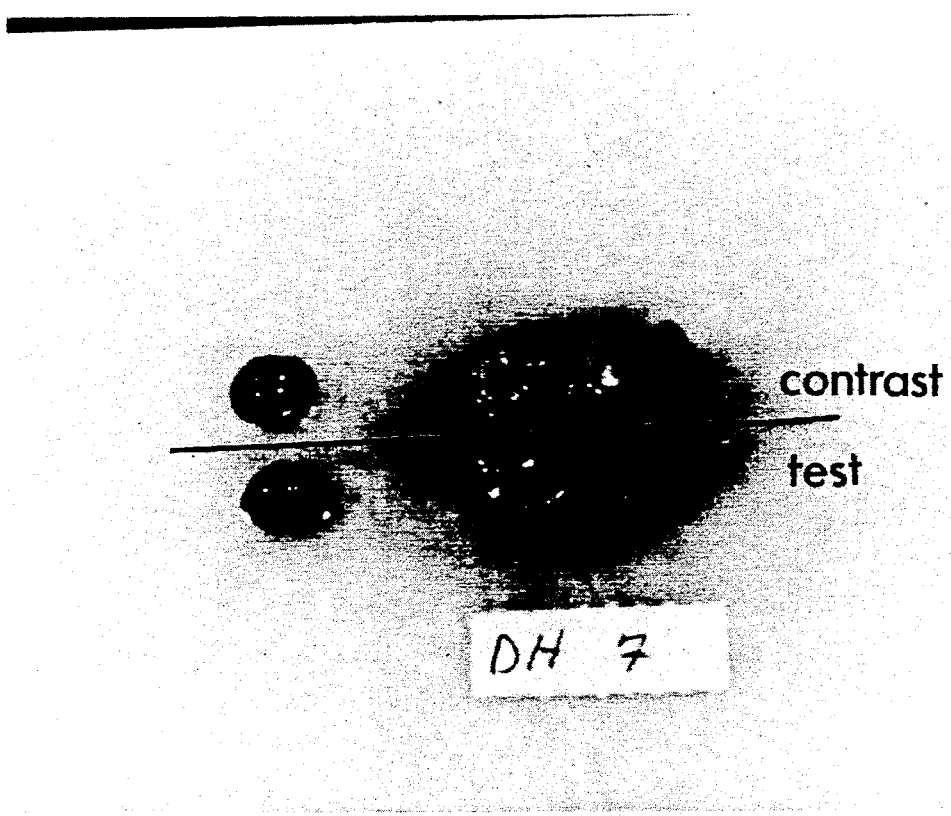
FIGS. 3(a) and 3(b) are photographs of body parts which illustrate effects produced by the use of compositions within the scope of the present invention.
Figure 3B:
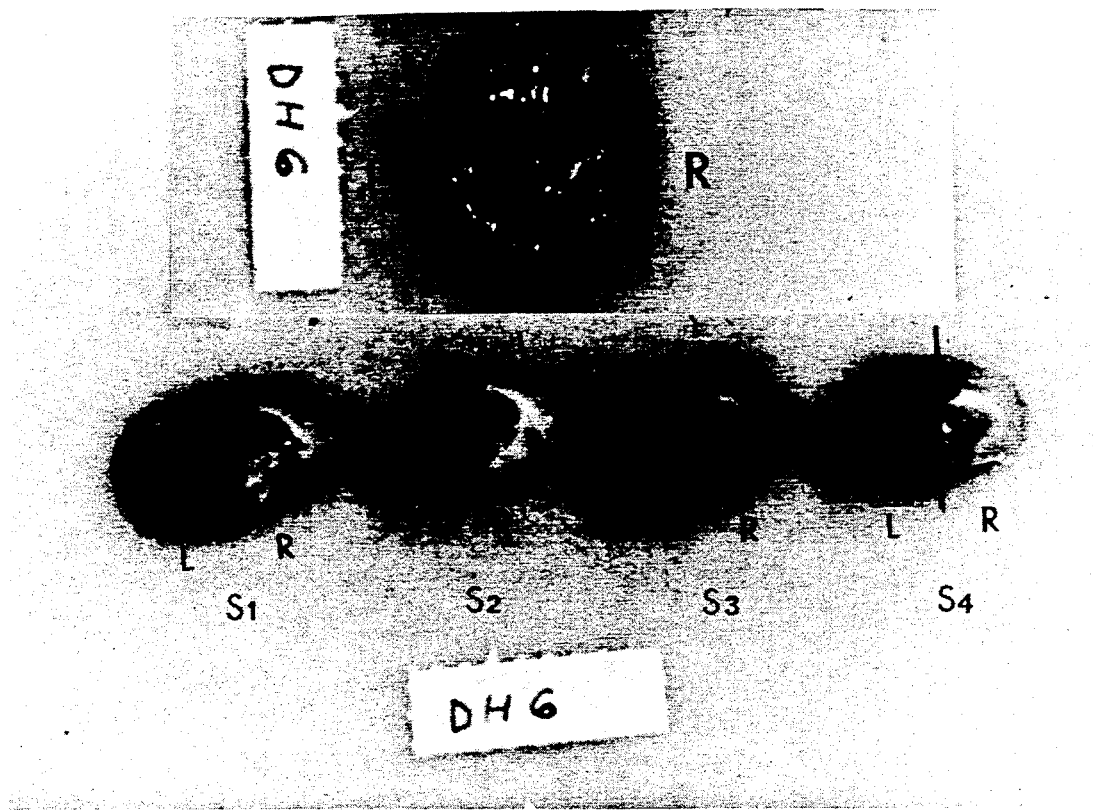

The objective of this study is to demonstrate the use of a blue dye as a marker penetrable into central nervous system (e.g. brain) with the addition of cyclopentadeconaolide in the infusion solution. One gram of cyclopentadecanolide was first dissolved in 0.5 ml absolute alcohol solution. The solution was then mixed with 10 ml of physiological saline-dye solution. The mixture was then filtered through a Millipore filter to remove excess amount of cyclopentadecanolide and thus a saturated cyclopentadecanolide solution was made for infusion. Three ml of the above solution was infused into the carotid artery of anethesized rats weighing about 250 grams. Cautions were taken to ensure that the infusion solution was entered into one side of the brain by clamping the other veins and arteries with surgical clips. The other side of the brain was used as a contrast. FIG. 3(a) shows that the tested side of the brain and the eye in the rat were deep blue in color due to the penetration of the blue dye enhanced by the use of cyclopentadecanolide; while the other side remained normal in color. FIG. 3(b) shows that the sections of the brain exhibit a deep blue color on the left or tested side; while the right or contrast side appears normal in color. S1 to S4 are four different sections of the brain. The results shown in FIGS. 3(a) and 3(b) indicate that the addition of cyclopentadecanolide to the infusion solution effects the penetration of chemicals through the blood brain barrier in rats.

TYPES OF MACROCYCLIC COMPOUND AS PERMEATION ENHANCER

Studies were performed to demonstrate that (1) the macrocyclic ketones containing more than 11 carbons possess unexpected desirable properties which are not possessed by those ketones having lower carbon content; (2) additional macrocyclic ketones such as e.g. muscone which has an alkyl group in the macrocyclic ring have similar enhancing properties; (3) other macrocyclic compounds such as cyclopentadecanolide which have an additional oxygen in the macrocyclic ring possess enhancing properties; (4) Another macrocyclic compound such as civetone which have unsaturated bond in the macrocyclic ring possess enhancing properties; (5) Other macrocyclic compounds such as ethylene brassylate which is the polyester of long chain dicarboxylic acid and ethylene glycol possess enhancing properties.

EXAMPLE 6

Comparison of different cyclic ketones for the enhancement of percutaneous absorption of drugs through hairless mouse skin.

Figure 4:
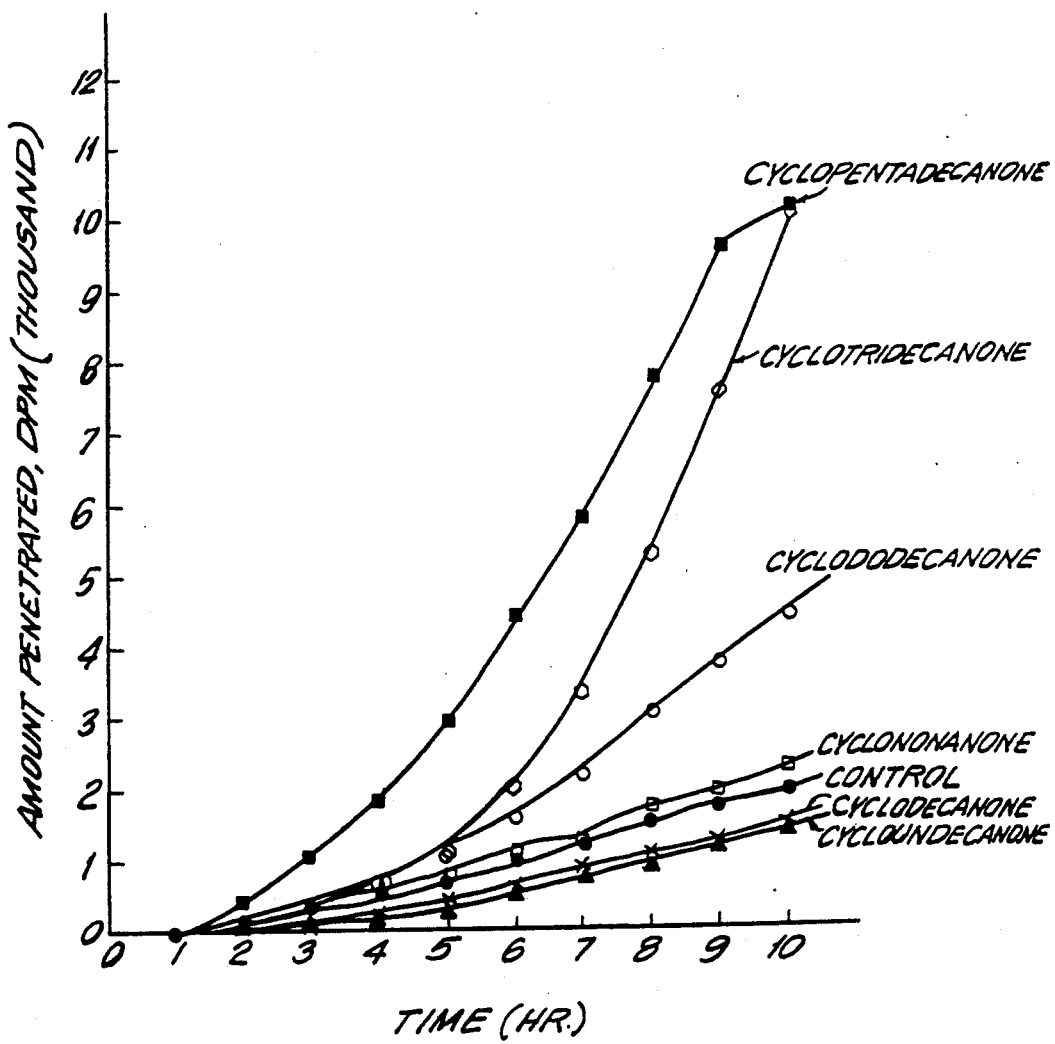

In this study, six different cyclic ketones were used for comparative studies on the percutaneous absorption of tritiated hydrocortisones through hairless mouse skin. These include cyclononanone (C9), cyclodecanone (C10), cycloundecanone (C11), cyclododecanone (C12), cyclotridecanone (C13), and cyclopentadecanone (C15). The preparation, penetration study, and data analysis of the experiment followed the procedure referred to in Example 1. For each compound, five skin samples were used for percutaneous absorption study. The concentration of enhancers used in the donor compartment was 2%. The duration of the experiment was performed for 10 hours when the steady-rate of penetration of drugs has been reached for at least several hours. FIG. 4 shows penetration profiles of hydrocortisone from percutaneous absorption enhanced by the different cyclic ketones through hairless mouse skin. The ranking of the potency of the enhanced absorption property of different cyclic ketones are in the following order: cyclopentadecanone > cyclotridecanone > cyclododecanone > cyclononanone > cycloundecanone > cyclodecanone (a decreasing order). The slope of the penetration profiles, which represent the steady state permeation rate of drugs, were calculated and shown in Table 5. The enhancement factor of different cyclic ketones was calculated based upon the control group as 100. There was a slight decrease in the permeation rate of hydrocortisone through hairless mouse skin when cyclodecanone and cycloundecanone were used as skin enhancers respectively. In other words, both cyclodecanone and cycloundecanone slightly inhibit the percutaneous absorption of hydrocortisone through hairless mouse skin. There was a little effect in the percutaneous absorption of hydrocortisone through hairless mouse skin when cyclononanone was used. There was a 230% increase in the permeation rate of hydrocortisone through hairless mouse skin when cyclododecanone was used in the study. However, there was a 524% increase and a 590% increase in percutaneous absorption of hydrocortisone through hairless mouse skin when cyclotridecanone and cyclopentadecanone were used as skin enhancers respectively. Additionally cyclopentadecanolide, a macrocyclic compound having an oxygen atom in the macrocyclic ring, was used in the same study for comparison. There was a 17-fold increase in percutaneous permeation rate of hydrocortisone through hairless mouse skin.

From this study, it was clearly demonstrated that (1) the cyclic ketones containing more than 11 carbon atoms possess unexpected, desirable properties which are not possessed by those ketones having a lower carbon content, (2) the higher the carbon number in the macrocyclic ring, the higher the enhanced permeation rate of hydrocortisone through hairless mouse skin.

TABLE 5

Comparison of permeation rat of hydrocortisone through hairless mouse skin by different cyclic ketones

| Chemical(s) | Permeation Rate (ug/cm*cm/hr) | Enhancement factor (%) |
|---|---|---|
| None or control | $5.25 \times 10^{-5}$ | 100 |
| cyclononanone | $5.96 \times 10^{-5}$ | 113 |
| cyclodecanone | $3.79 \times 10^{-5}$ | 72 |
| cycloundecanone | $3.91 \times 10^{-5}$ | 74 |
| cyclododecanone | $1.21 \times 10^{-4}$ | 230 |
| cyclotridecanone | $2.75 \times 10^{-4}$ | 524 |
| cyclopentacanone | $3.10 \times 10^{-4}$ | 590 |
| cyclopentadecanolide | $8.94 \times 10^{-4}$ | 1703 |

1. The concentration of chemical used in the donor compartment was 2%.
2. Permeation rates were calculated from the slope of permeation profile.
3. The enhancement factor was calculated based upon the control group (without chemical) as 100.

EXAMPLE 7

The procedure of example 1 was repeated except that the only adjuvant tested was cyclopentadecanone at concentrations of 0.5, 1, 2, 3, 5 and 10% w/v. From 0.2 to 0.9 ml of methanol was added to 2.7 ml of the solution to help dissolve the ketone in the propylene glycol at higher concentrations. The presence of methanol did not appreciably change the permeability of the skin as demonstrated by the profile obtained with the control sample containing methanol. The penetration profiles are shown in FIG. 5, and it can be readily seen that the minimal effective concentration of the adjuvant was 2%.

Figure 5:
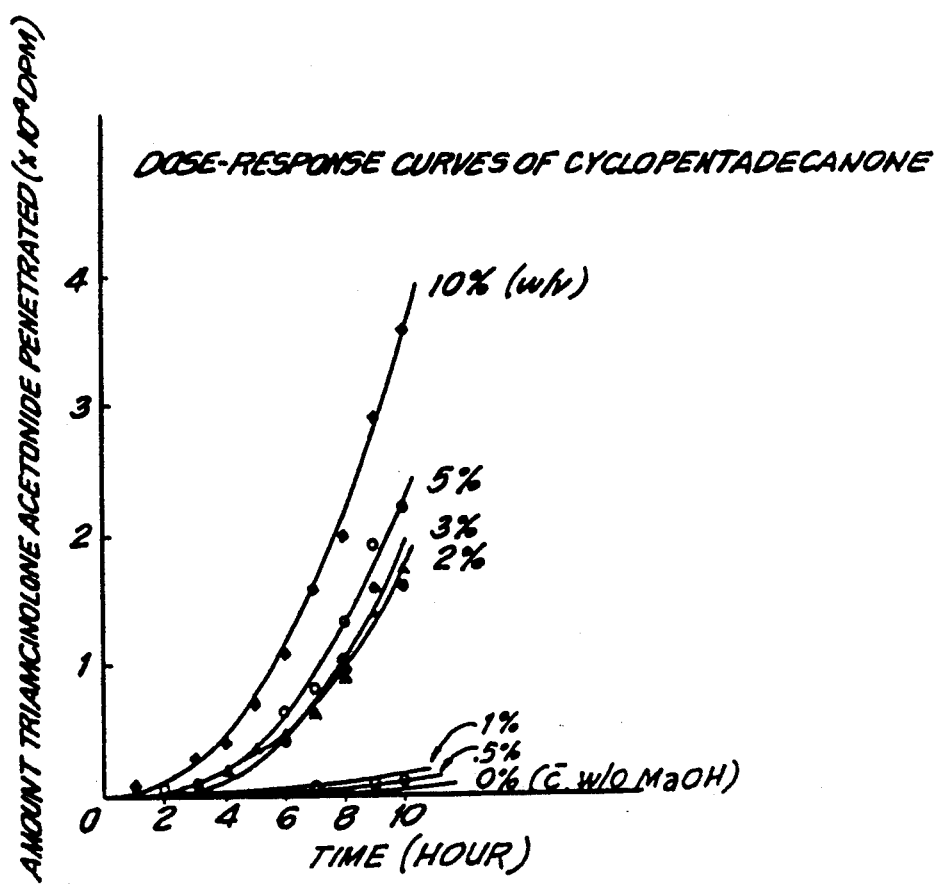

Based upon the data presented in FIG. 5, the rates of flux calculated from the linear portion of the curve are given in Table 6.

TABLE 6

| Concentration of Adjuvant | Flux (dpm/cm²/hr) | Ratio (%) |
|---|---|---|
| 10 | $7.4 \times 10^3$ | 4625 |
| 5 | $4.1 \times 10^3$ | 2563 |
| 3 | $3.7 \times 10^3$ | 2310 |
| 2 | $3.7 \times 10^3$ | 2310 |
| 1 | $0.31 \times 10^3$ | 200 |
| 0.5 | $0.31 \times 10^3$ | 100 |
| 0 (Control) | $0.16 \times 10^3$ | 100 |

Studies with Oxacyclohexadecan-2-one or cyclopentadeconolide

EXAMPLE 8

Solution

Sample preparation, permeation study and data analysis were carried out using the same procedures as Example 1. The drug used is triamcinolone acetonide and the concentration of cyclopentadeconaolide is 2%.

Figure 6:
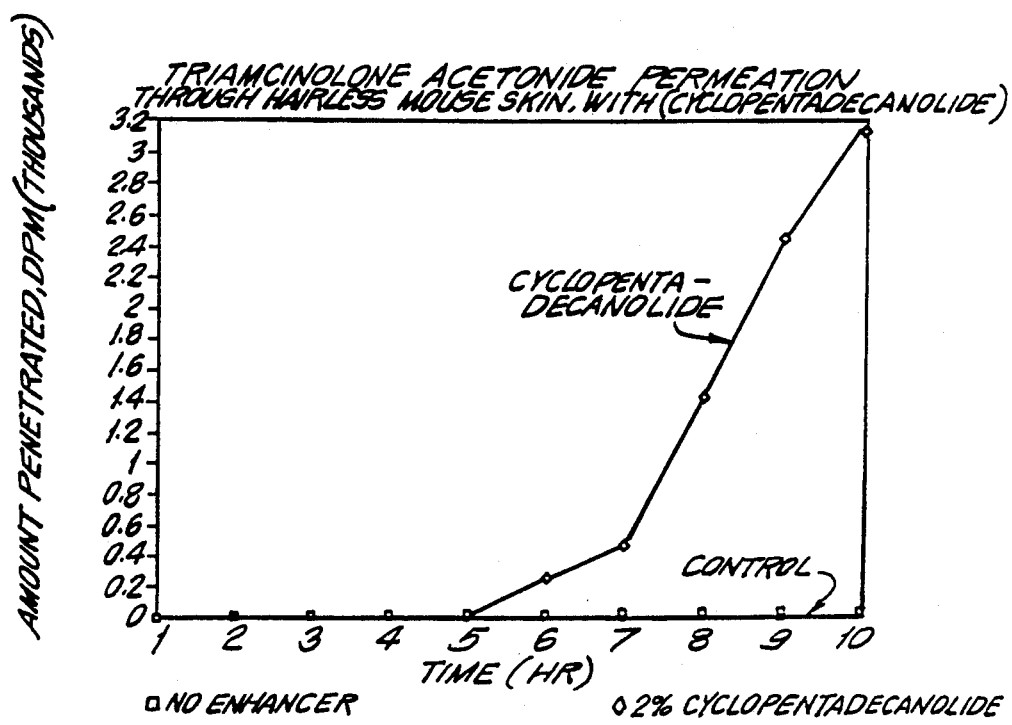

FIG. 6 shows the permeation profiles of tritiated triamcinolone acetonide with cyclopentadeconolide. Without the addition of cyclopentadecanolide, no penetrated drug was detected in the receptor compartment. However, when cyclopentadecanolide was used at the level of 2%, the drug, triamcinolone acetonide penetrated through hairless mouse skin. From the permeation profile, four permeation parameters, i.e., lag time, permeability coefficient of membrane (Kp), diffusion constant within membrane (D), and partition coefficient between membrane and vehicle (Km) were analyzed and listed in Table 7.

TABLE 7

Triamcinolone acetonide penetration parameters with and without cyclopentadecanolide

| Enhancer | Lag time (hr) | KP (cm/hr) | D (cm²/hr) | Km |
|---|---|---|---|---|
| None | — | — | — | — |
| cyclopentadecanolide (2%) | 6.03 | 3.88 | $4.42 \times 10^{-7}$ | $3.51 \times 10^4$ |

EXAMPLE 9

Cream

In a separate set of experiments, the formulations were of aqueous emulsion of cyclopentadeconolide in saline or buffer with Tween 20 as an emulsification agent. Cyclopentadecanolide in the desired amount was combined with Tween 20 and saline, in a 40° C. water bath/sonicator and emulsified by sonication. In this set of experiments the enhancement of hydrocortisone penetration through hairless mouse and human cadaver skin was examined. The range of cylcopentadeconolide concentration was 0.001-10%. A predetermined concentration of enhancer was combined with radiolabelled tritiated hydrocortisone in saline at a concentration of 0.05 mM. Tween 20 (1 or 0.1%) was placed in the donor compartments to emulsify the enhancer. The receiver compartments were filled with saline.

Figure 7:
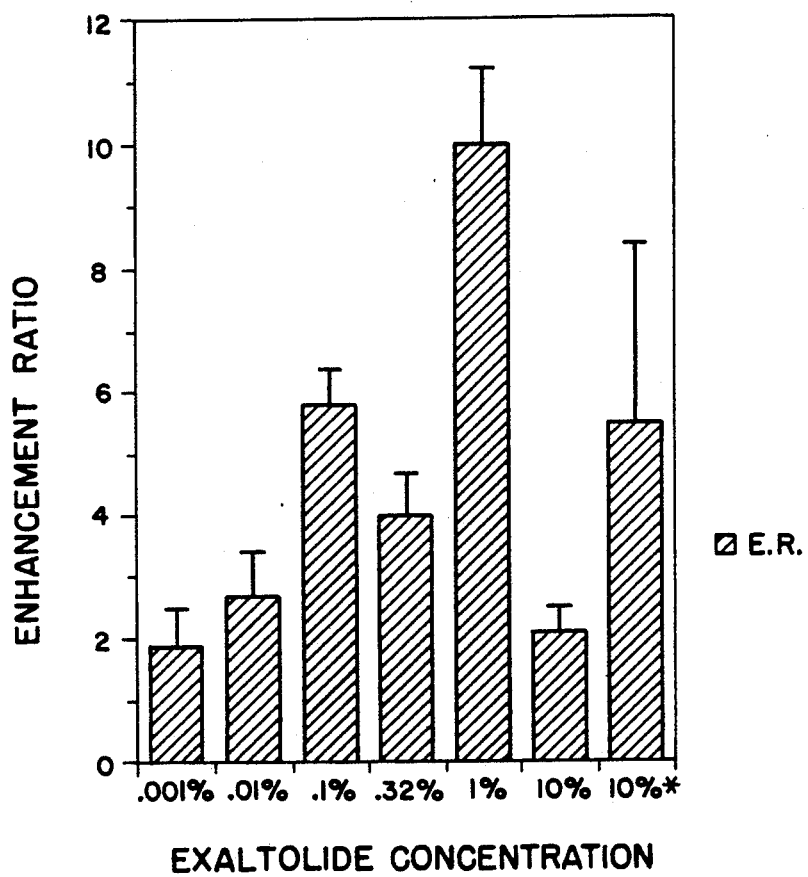
FIGS. 7, 8, and 11 are graphical representations showing the effects of use of compositions within the scope of the present invention.
Figure 8:
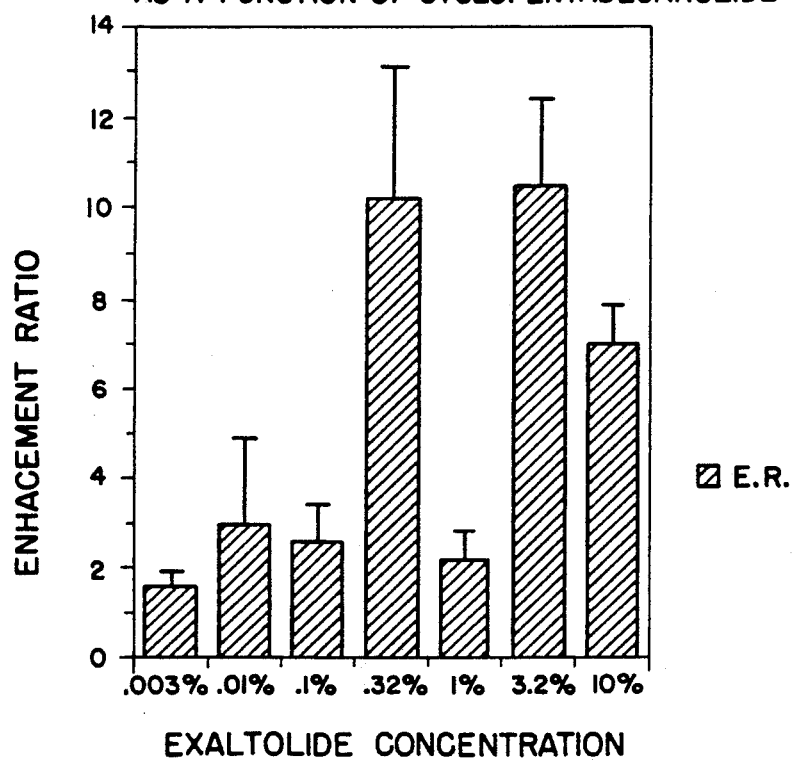

FIGS. 7 and 8 depict the effect of cyclopentadeconolide on hydrocortisone permeation as a function of enhancer concentration. Studies with hairless mouse skin are shown in FIG. 7 where the concentration of cyclopentadeconolide spans 0.001% to 10%. Enhancement of hydrocortisone transport was detected as low as 0.001%, although the difference from the permeability of the controls was not significantly different at the 90% confidence level. The enhancement ratio was greatest at 1% cyclopentadecanolide. FIG. 8 contains a similar concentrational dependency study with human cadaver skin. Significant (with 90% confidence) enhancement was detected at 0.003% cyclopentadecanolide with maximum enhancement occurring at 0.32% and 3.2% cyclopentadecanolide. For both hairless mouse cadaver and human cadaver skin, the magnitude of enhancement ranged from about 2 to 10; furthermore, it appeared that both skin types were comparably sensitive to cyclopentadecanolide effect.

Spray

The illustration, previously shown in Example 2, explains the use of cylclopentadecanolide in the nasal spray of insulin for the reduction of blood glucose in dogs. Similarly, Example 3 illustrates that cyclopentadecanolide can be used in the nasal spray formulations for the treatment of Type II diabetes in humans.

EXAMPLE 10

Civetone, 9-cycloheptadecen-1-one

Sample preparation, permeation study and data analysis were carried out following the procedure referred to in Example 1. The enhancer used in this study is civetone at the level of 2% in the solution of donor compartment of diffusion cell.

Figure 9:
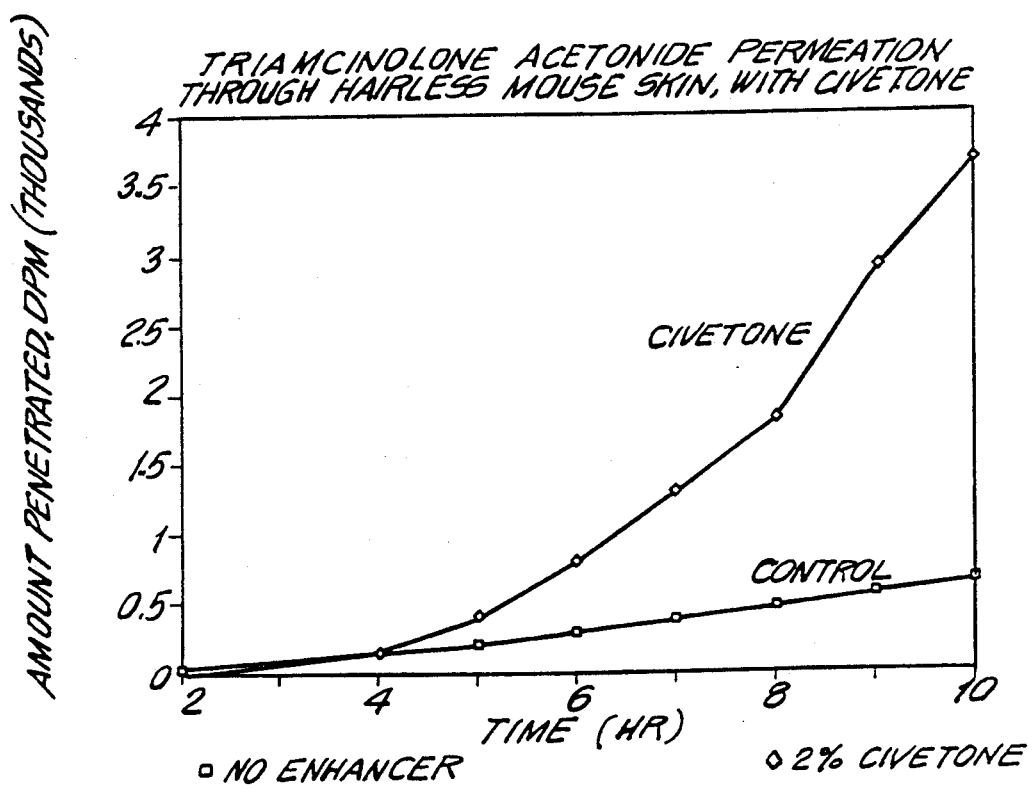

FIG. 9 shows the permeation profile of tritiated triamcinolone acetonide through hairless mouse skin with and without civetone. The steady-rate permeation rate, calculated from the slope of permeation profile, was $8.36 \times 10^{-3}$ ug/cm *cm/ hr with civetone; while it is only $1.10 \times 10^{-3}$ ug/cm *cm/hr without civetone. There was a 760% increase in the percutaneous permeation rate of triamcinolone acetonide when civetone was used as skin enhancer at the level of 2%.

EXAMPLE 11

Ethylene Brassylate or Ethylene undecane dicarbosylate

Figure 10:
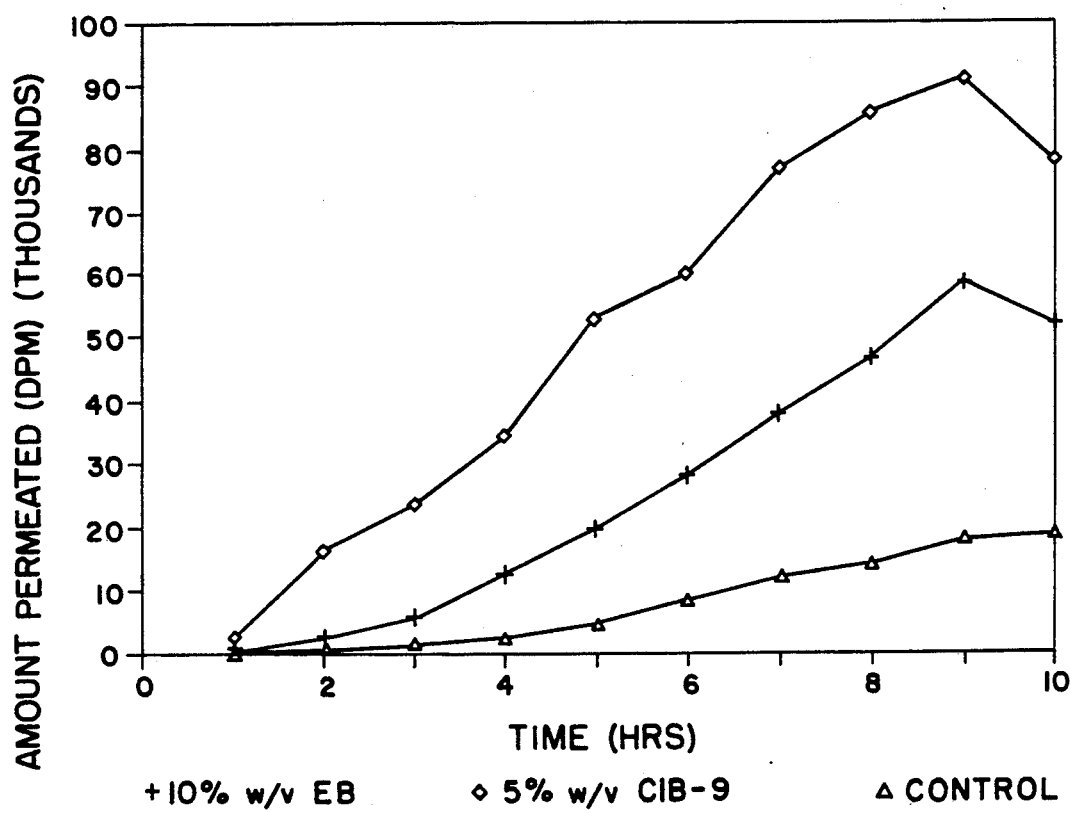

The preparation of skin, permeation study, and data analysis follow the methods illustrated in Example 1, except that the drug used is propranolol HCl and the permeation enhancer used is ethylene brassylate at the 10% concentration. The permeation rate of tritiated propranolol HCl through hairless mouse skin enhanced with 10% ethylene brassylate is 15.8 ug/cm*cm/hr, while the permeation rate of tritiated propranolol without enhancer is 5.05 ug/cm*cm/hr. There is a 3-fold increase in steady state permeation rate when ethylene brassylate is added. Simultaneously, 5% cyclopentadecanolide is used as a positive control. The steady state permeation rate is 24.8 ug/cm*cm/hr, a 5-fold increase. FIG. 10 shows the penetration profile of tritiated propranolol HCl enhanced by ethylene brassylate and cyclopentadecanolide, respectively. Table 8 lists the penetration parameters i.e. lag time, partition coefficient for the vehicle to the membrane, diffusion coefficient, and permeability coefficient within the membrane analyzed from the penetration profile presented in FIG. 10.

TABLE 8

| | PERMEATION PARAMETERS OF PROPRANOLOL | | | |
|---|---|---|---|---|
| | T hr | Kp cm/hr | D cm*cm/hr | Km |
| Control | 2.06E + 00 | 1.17E − 02 | 1.29E − 06 | 3.63E + 01 |
| 10% V/V Ethylene Brassylate | 1.80E + 00 | 3.68E − 02 | 1.48E − 06 | 9.95E + 01 |
| 5% W/V Cyclopentadecanolide ENHANCER | 7.20E − 01 | 5.75E − 02 | 3.70E − 06 | 6.21E + 01 |

EXAMPLE 12

Figure 11:
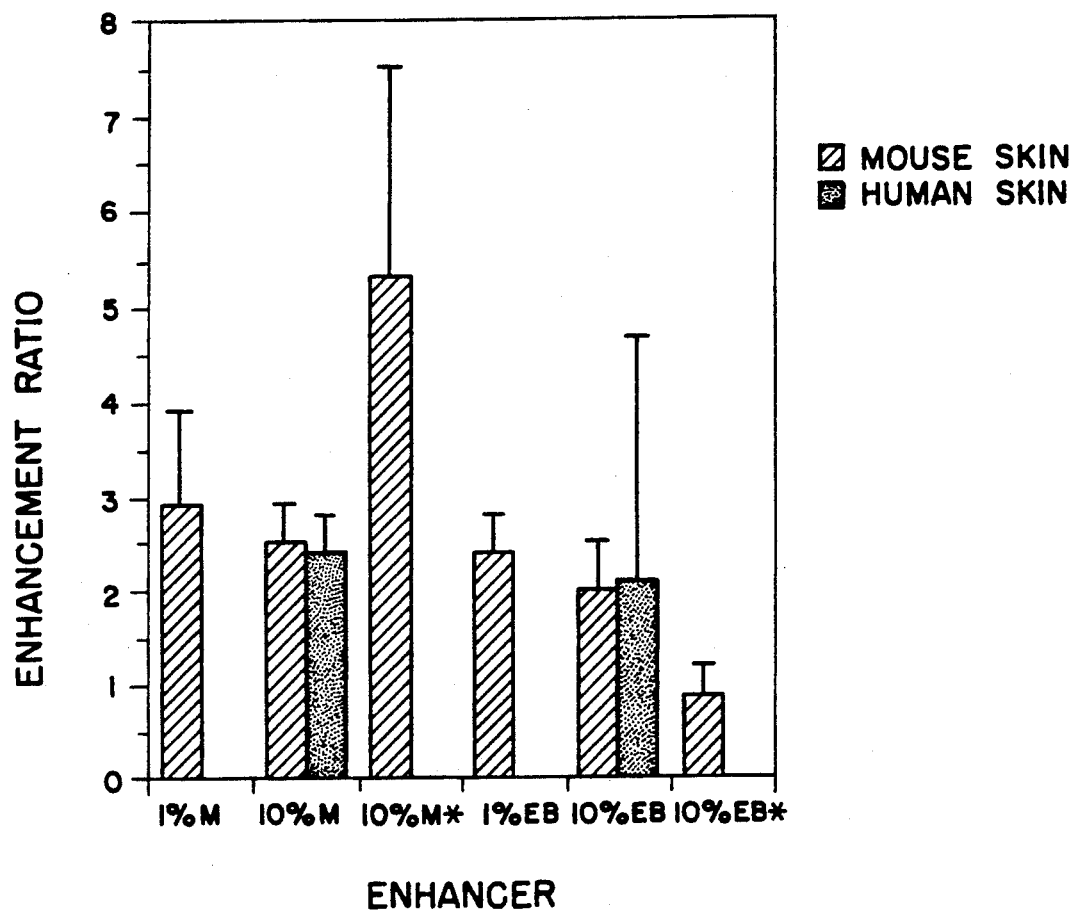

In a separate study, a cream formulation containing tritiated hydrocortisone and ethylene brassylate was used. The content of the formulation was the same as Example 9, except for the replacement of the enhancer. FIG. 11 shows the enhancement ratio of hydrocortisone by 3-methyl cyclopentadecanone and ethylene brassylate as a function of skin type. It shows that percutaneous absorption of hydrocortisone can be enhanced by a 5.5-fold and 2.5-fold increase with 10% 3-methyl cyclopentadecanone and 10% ethylene brassylate respectively. The results obtained from examples 6 to 12 clearly indicate that macrocyclic compounds including macrocyclic ketones with or without alkyl group, macrocyclic lactones, and polyesters of ethyelene and dicarboxylic acids, possess the property of enhancing the rate of passage of drugs through skin, nasal membranes, and other biological membranes.

TYPES OF THERAPEUTIC DRUGS

Examples 13 to 20 illustrate the uses of macrocyclic compounds as permeation enhancers for different types of therapeutic agents. These include anti-hypertensive drugs such as clonidine and propranolol, anti-sedative drugs such as diazepam, steroidal hormones such as estradiol, steroidal anti-inflammatory drugs such as glucocorticoids, hydrocortisone, or triamcinolone acetonide, non-steroid anti-inflammatory drugs such as indomethacin, anti-psoriasis drugs such as psoralen, calcium blockers such as verapramil, anti-diabetic drugs such as insulin, estrus synchronizing agent such as progestin, contraceptives such as estradiol, and so on. Other types of drugs whose rate of transdermal or transmembrane passage would be increased include, but not limited to, antibiotics, antifungal agents, CNS depressants, and sunscreens.

EXAMPLE 13

Percutaneous Absorption of Triamcinadone Acetonide

The procedure of example 1 was repeated except that 3-methyl-cyclopentadecanone was used as the adjuvant and 0.1 to 0.3 ml ethanol was added to the solution to completely dissolve the adjuvant. This amount of ethanol did not appreciably change the permeability of the skin as demonstrated by the profiles of the controls with and without ethanol. The penetration profiles are shown in FIG. 12, and it can be readily seen that the minimal effective concentration of the adjuvant is 2%.

Figure 12:
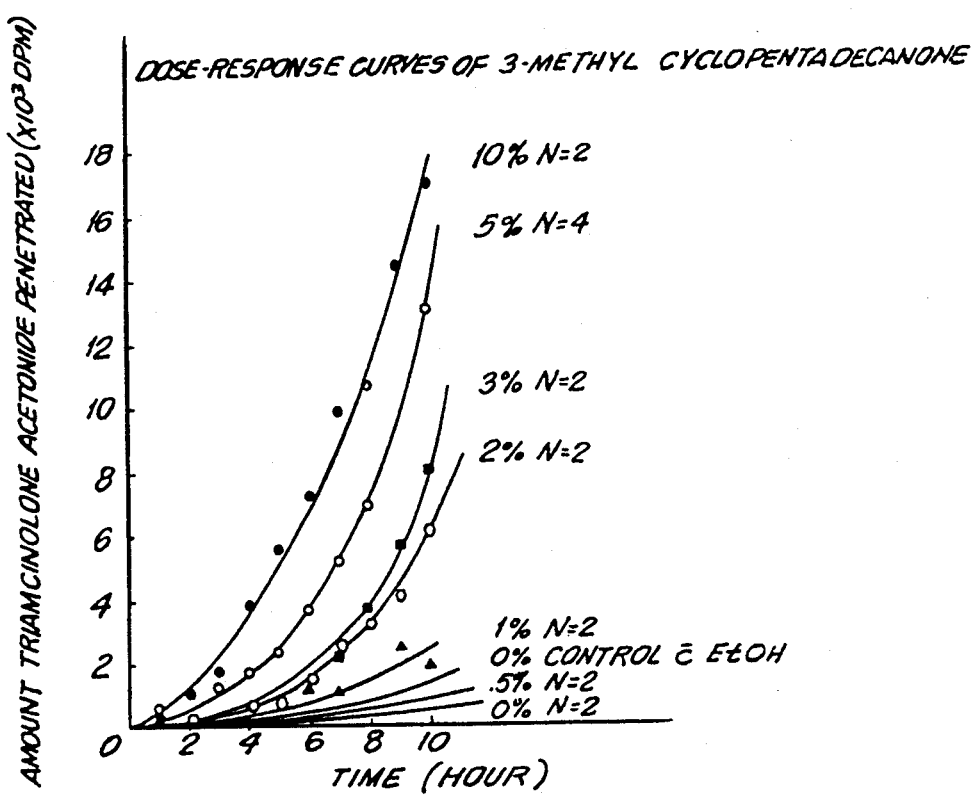

Based upon the data presented in FIG. 12 the rates of flux calculated from the linear portions of the curves are given in Table 9.

TABLE 9

| Concentration % | Flux (dpm/cm²/hr) | Ratio (%) |
|---|---|---|
| 10 | $0.3 \times 10^3$ | 3000 |
| 5 | $0.3 \times 10^3$ | 3000 |
| 3 | $0.22 \times 10^3$ | 2200 |
| 2 | $0.15 \times 10^3$ | 1500 |
| 1 | $0.10 \times 10^3$ | 1000 |
| 0.5 | $0.013 \times 10^3$ | 130 |
| 0% (with ethanol) | $0.025 \times 10^3$ | 250 |
| 0% (no ethanol) | $0.010 \times 10^3$ | 100 |

EXAMPLE 14

Percutaneous Absorption of Psoralen

The procedure of example 1 was repeated except that the drug was 8-methoxy-psoralen (MOP) with a concentration of 46 mg/ml used as $H^3$-MOP dissolved in propylene glycol, and the adjuvants tested were 3-methylcyclopentadecanone (I) (0.4% w/v) and cycloundecanone (III) (2% w/v). The penetration profiles are shown in FIG. 13.

Figure 13:
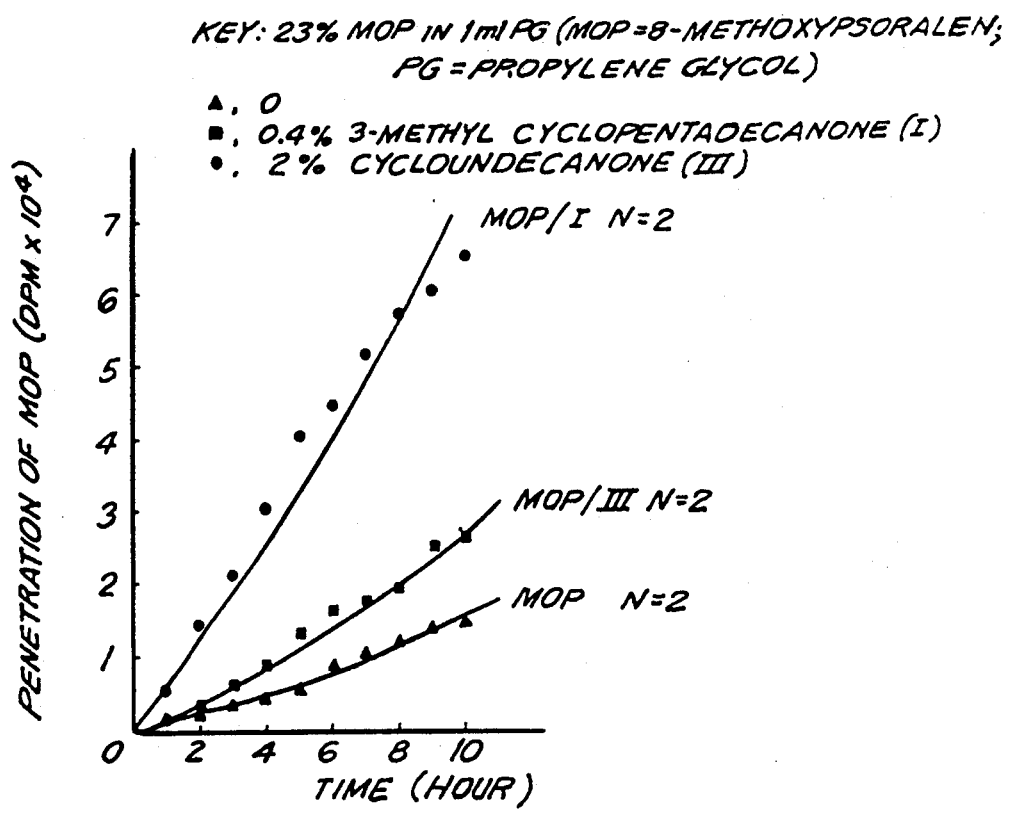

Based upon the data presented in FIG. 13, the rates of flux calculated from the lines portion of the curves are shown in Table 10.

TABLE 10

| Adjuvant | Flux (dpm/cm²/hr) | Ratio (%) |
|---|---|---|
| Control | $1.88 \times 10^3$ | 100 |
| 0.4% I | $8.13 \times 10^3$ | 432 |
| 2% III | $3.63 \times 10^3$ | 193 |

EXAMPLE 15

Percutaneous Absorption of clonidine

Figure 14:
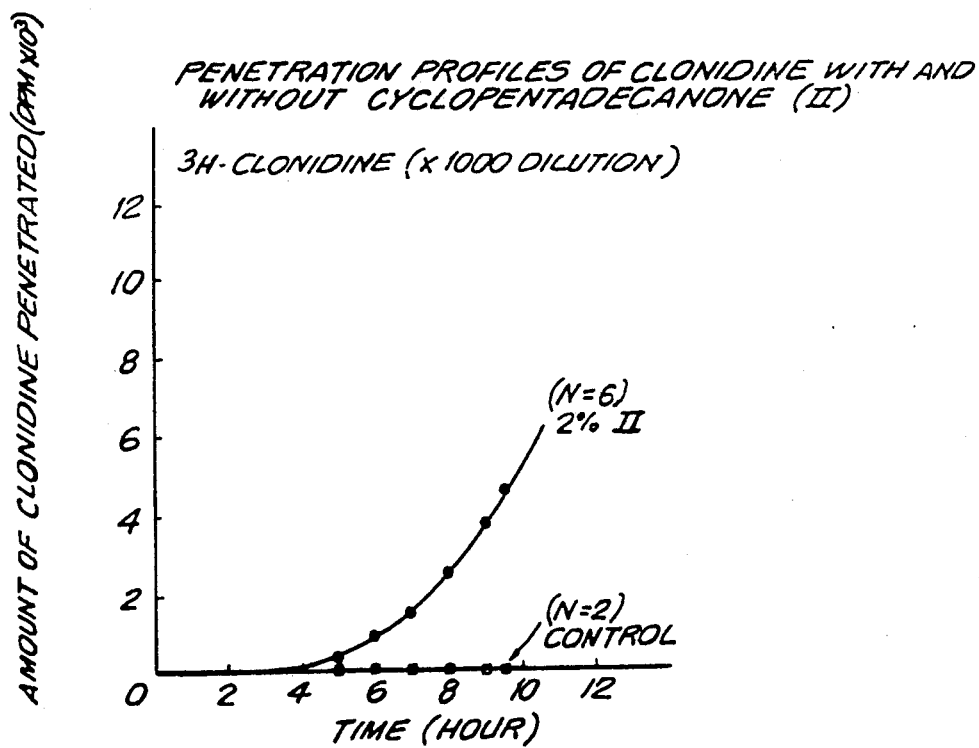

The process of example 1 was repeated except that tritiated clonidine, diluted 1000 fold with cold clonidine was used. The tests were run with a propylene glycol containing 37.4 mg/ml clonidine and 2% (w/v) cyclopentadecanone. The penetration profiles are shown in FIG. 14. Based on the profile the flux of the preparation containing the adjuvant was 10.1 mg/cm²/hr or equivalent to $1.83 \times 10^6$ dpm/cm²/hr of the respective radioisotopically labeled drug.

EXAMPLE 16

Percutaneous Absorption of Diazepam

Figure 15:
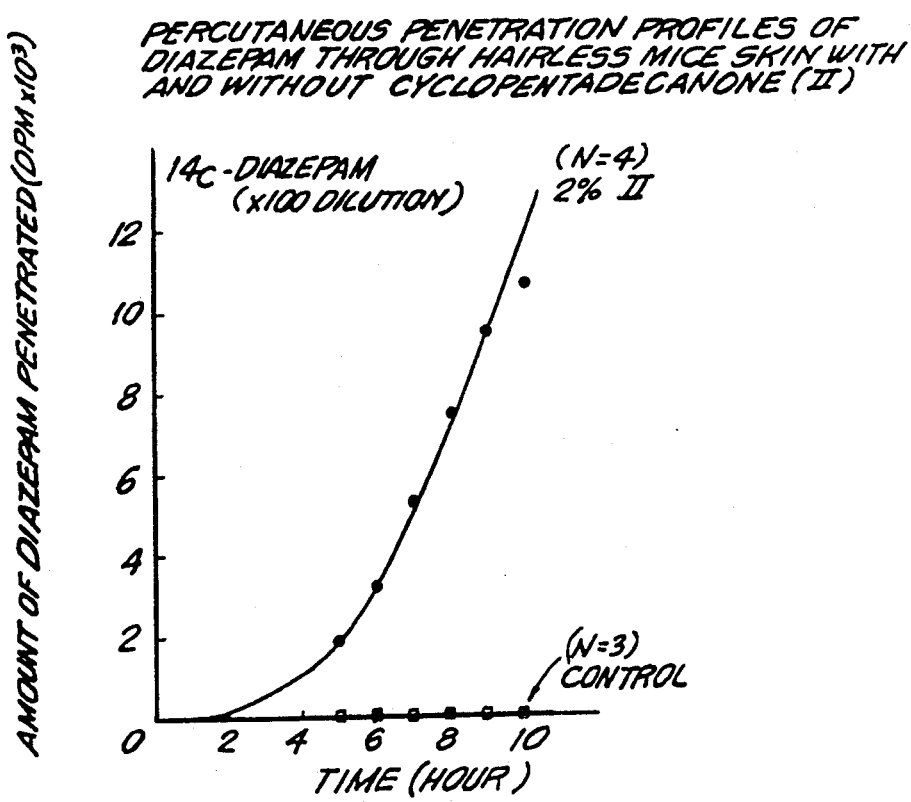

The procedure of example 15 was repeated except that $^{14}C$ diazepam, diluted 100 fold with cold diazepam, was used. The tests were run with a propylene glycol solution containing 1.91 mg/ml of diazepam and 2% (w/v) cyclopentadecanone. The penetration profiles are shown in FIG. 15.

EXAMPLE 17

Percutaneous Absorption of Diazepam

Figure 16:
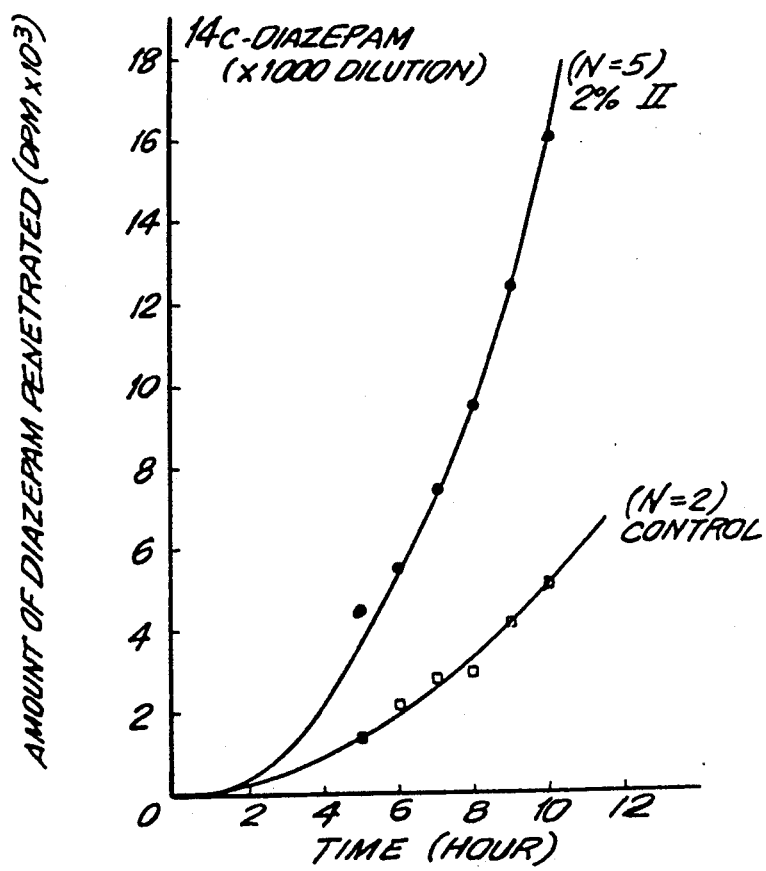

The procedure of example 15 was repeated except that $^{14}C$ diazepam, diluted 1,000 fold with cold diazepam, was used. The propylene glycol solution contained 18.9 mg/ml of diazepam and 2% (w/v) of cyclopentadecanone. The penetration profiles are shown in FIG. 16.

EXAMPLE 18

Percutaneous Absorption of Estradiol

Figure 17:
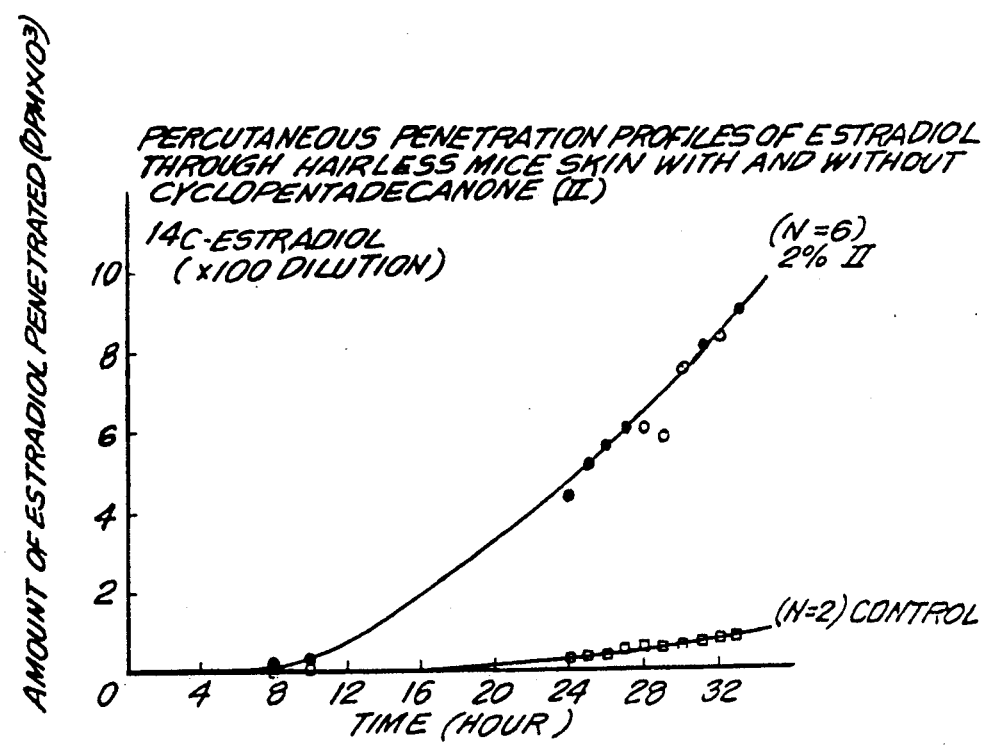

The procedure of example 15 was repeated except that $^{14}C$ estradiol, diluted 100 fold with cold estradiol, was used. The tests were run with a propylene glycol solution containing 1.06 mg/ml estradiol and 2% (w/v) cyclopentadecanone. The penetration profiles are shown in FIG. 17.

EXAMPLE 19

Percutaneous Absorption of propranolol

Figure 18:
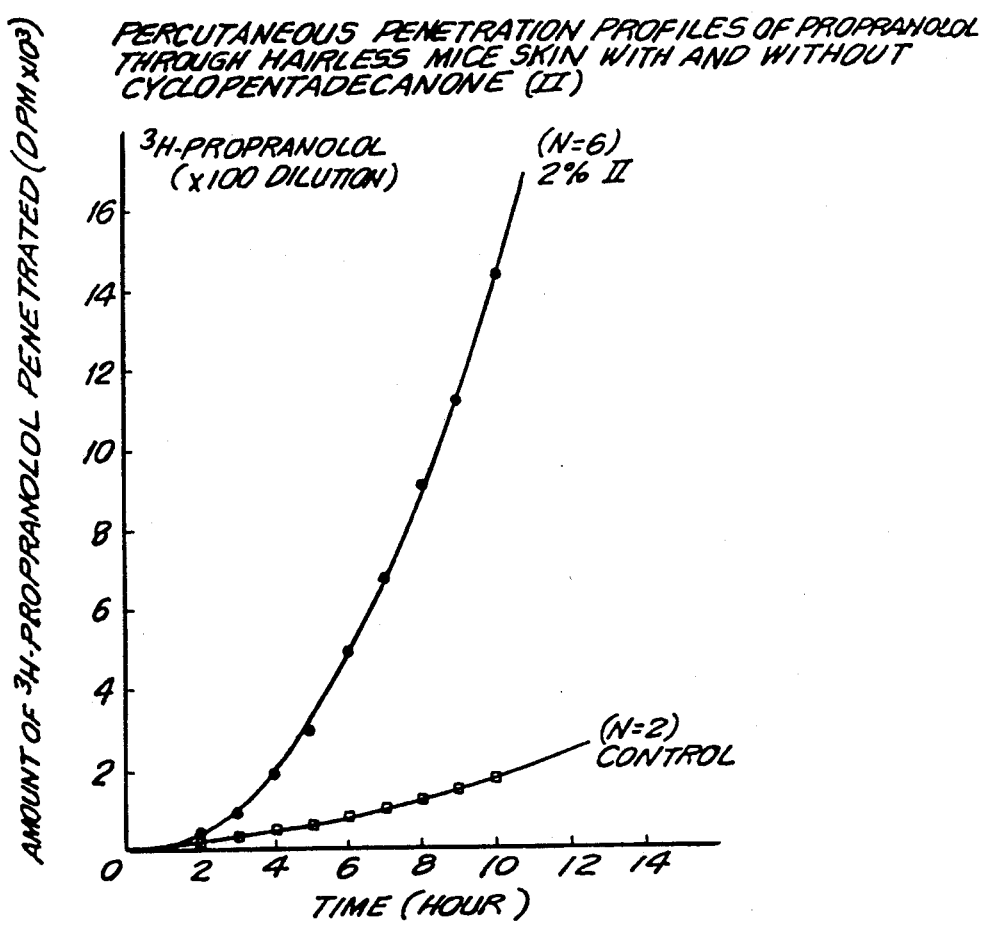

The procedure of example 15 was repeated except that tritiated propranolol diluted 100 fold with cold propranolol, was used. The tests were run with a propylene glycol solution containing $9.7 \times 10^{-3}$ mg/ml propranolol and 2% (w/v) cyclopentadecanone. The penetration profiles are shown in FIG. 18.

EXAMPLE 20

Percutaneous Absorption of Verapramil

Figure 19:
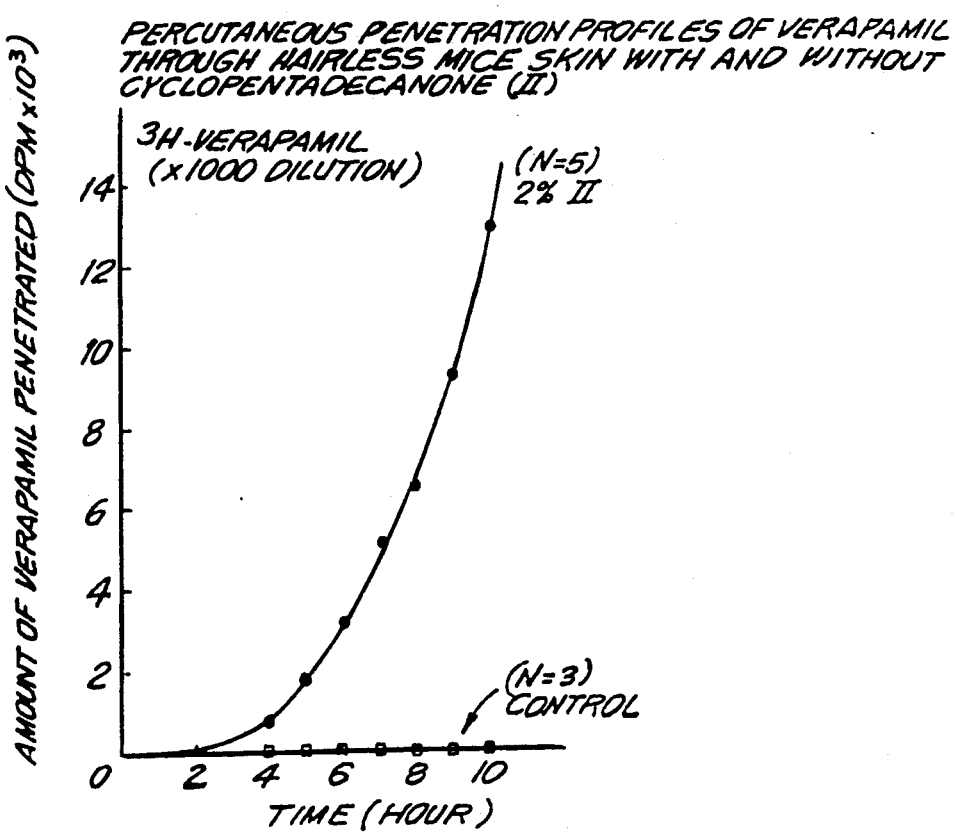

The procedure of example 15 was repeated except that tritiated verapramil, diluted 1000 fold with cold verapramil, was used. The tests were run with a propylene glycol solution containing $1.54 \times 10^{-2}$ mg/ml verapramil and 2% (w/v) cyclopentadecanone. The penetration profiles are shown in FIG. 19.

Examples 21 and 22 relate to the use of enhancers in drug compositions that are applied using a transdermal patch or similar delivery system. In particular, studies were conducted with respect to the compatibility of the enhancers with polymers used in these patches, such as silastic elastomers or pressure sensitive adhesives made by Dow Corning Corporation, Midland, Mich. The methods of evaluation are described below:

A. Preparation of adhesives solution: The appropriate quantity of adhesive solution was weighed and added to a known weight of cyclopentadecanone so as to provide results in the 0, 1, 5, 20 or 30 wt % (w/w) of cyclopentadecanone (permeation enhancer) in the dry adhesive (100% solids) following coating.

B. Machine Coating Laminates: The adhesive solution was coated onto Scotchpak 1022 release liner (manufactured by 3M Company, St. Paul, Minn.) with a custom fabricated Meyer bar (40 threads/inch, depth 0.003") at a speed of 165 inches/minute with a setting of 5.5 on the motor scale, onto release liner (2 mil thick) and allowed to air dry for a minimum of 30 minutes. The base was cleaned with Freon PCA following coating of the adhesive solution. The cast adhesive was allowed to dry at room temperature to allow the Freon PCA to evaporate. A sheet of polyester was then transfer-coated using IPA and a squeeze, then a 4.5 lb rubber roller. These resulted in a 1 and 2 mil thick layer of 355 BIO-PSA(R) Medical Grade Adhesive and X-7-2920 BIO-PSA(R) Amine Resistant Medical Grade Adhesive, respectively.

C. Testing of Laminates: The tape properties of laminates were tested initially (after a minimum of 24 hours after preparation) or after two weeks of aging at room temperature (20 to 25 degree C.).

D. Measurement of Tape properties:

D.1. Surface tack measurement: Pressure sensitive adhesives have the ability to form a bond with another surface during a short contact time under low pressure. This general phenomenon is known as tack or quick stick. The strength of the bond depends upon the application pressure, dwell time, and the rate of withdrawal. Quantitative tack measurements were performed through use of a Polyken (Tm) brand Probe Tack Tester (Testing Machines, Inc. Amityville, N.Y). Briefly summarized, tack measurements, expressly of 0.5 cm/sec., a contact pressure of 100 grams cm2, and contact time of 0.5 cm/seconds. The method is based on ASTM D-2979. Adhesive laminates were cut into 2.5 cm$\times$2.5 cm pieces. A test sample was placed on the tester with the "donut" shaped weight on top of it. The maximum force was recorded ($n=5$) for replicate samples. The probe was wiped with a lint-free material dipped in acetone after each series of five pieces. The probe was allowed to stand for at least 2 seconds after being wiped with a dry cloth to air dry. The average of these readings and the standard deviation were reported.

D.2. Peel/Release Adhesion (Peel Force): The resistance of an adhesive tape to a peeling force is known as the peel adhesion or the release. The peel values reported were obtained in a manner similar to that used to test adhesion. Adhesive laminates were prepared and cut into one-inch wide strip of laminated release liner (SCOTCHPAK(R) 1002(R), adhesive, and MYLAR(R) polyester film). The release liner was stripped at a rate of 40 inches/minute at an angle of 180 degrees while attached to a tensile testing machine, with the results expressed in grams per centimeter. An average value over the entire panel was recorded. Data were expressed as the mean $+/-$ SD ($n=3$).

D.3. Adhesion Force: the adhesion force with respect to a stainless steel test panel was determined. Quantitative adhesion measurements reported were obtained through use of a one-inch wide MYLAR(R) polyester tape coated with a layer of adhesive. The tape was adhered to a stainless steel panel with a 4.5 lb. roller and stripped attached to a tensile testing machine, with the results expressed in grams per centimeter. Between each run, test panels were cleaned with acetone and trichloroethylene and allowed to air dry. Data were expressed as the mean $+/-$ S.D. ($n=3$) unless otherwise specified.

D.4 Interpretation of Tape Property Tests: An arbitrary minimum value for tack ($>50$ g/cm2) and adhesion, ($>200$ g/cm) and maximum value for peel $<50$ g/cm were used as a criterion to determine the suitability of tape properties of the test samples for use in a transdermal drug delivery system.

EXAMPLE 21

The purpose of this study was to determine the compatibility of cyclopentadecanone (0, 1, 5, and 10 wt %), a skin penetration enhancer in comparison with other selected enhancers including: Azone (R), ethanol, isopropyl myristate, isopropyl palmitate, and eucalyptol, on the tape properties (i.e. peel, subsequent adhesion, and tack) of 355 BIO-PSA(R) and x7-2920 Amine Resistant BIO-PSA(R) Medical Grade Silicone Pressure Sensitive Adhesives and the effect of these enhancers on tape properties were evaluated initially under various aging conditions.

355 BIO-PSA(R) has been used and x7-2920 Amine Resistant BIO-PSA(R), has been developed for use in transdermal drug delivery system and reported by Huie, Schmidt, and Warren in Testing Adhesive and Liner for Transdermal Drug Delivery, Adhesive Age, June issue 1985 and also by Krug and Marecki in Porous and Other Medical Pressure Sensitive Adhesives, Adhesives Age, November issue page 19–23, 1983.

Tables 11 to 13 illustrated the use of enhancers in the transdermal drug delivery systems and the effect of loading on the initial tape properties. The cyclopentadecanone was soluble in the adhesive prior to casting. Laminates containing 10 wt % cyclopentadecanone were clear. Slight and marked crystallization were observed in laminates containing 20 and 30 wt % cyclopentadecanone indicating that the level of solubility of cyclopentadecanone in 355 adhesive solids was between 10–20 wt %.

The tack and tape properties of the 10 wt % cyclopentadecanone laminates were similar to 355 control laminates. The compatibility of 0, 1, 5, and 10 wt % levels of cyclopentadecanone in comparison with other enhancers on the initial tape properties of DC 355 pressure sensitive adhesive (PSA) are shown in TABLE 11. The initial peel force of all laminates containing up to 10 wt % of each enhancer was low ($<10$ g/cm) and acceptable for a transdermal drug delivery system. Cyclopentadecanone was found to increase the peel force, and reduce adhesion proportional to its loading level in both DC 355 and X7-2920 pressure sensitive adhesives. A maximum loading level of 10 wt % cyclopentadecanone was considered to be compatible with both DC 355 (TABLE 11) and x7-2920 BIO-PSA(R) (TABLES 12 and 13).

Ethanol did not adversely affect tape properties of either DC 355 (TABLE 11) or X7-2920 BIO-PSA (TABLES 12 and 13) at levels of 10 wt %; however, the low alcohol most likely evaporated due from time of tape preparation to time of testing. The concentrations of ethanol in the tested tape probably are negligible.

Azone(R), isopropyl palmitate, and isopropyl myristate appeared to be soluble in both PSA's at levels of 10 wt %; however, they plasticized the adhesive resulting in cohesive failure (i.e. transfer of adhesive to release liner, leaving residue after peel, residue on adhesion test panels, and acted as a solvent for the adhesives).

The maximum compatible levels of these enhancers with both 355 and X7-2920 BIO-PSA(R) were isopropyl palmitate (1 wt %), isopropyl myristate (5 wt %), Azone (R) (1-2 wt %), eucalpyptol ($<5$wt %).

In short, cyclopentadecanone can be incorporated into silicone pressure sensitive adhesives at higher levels than other penetration enhancers without compromising tape properties and thus, can be considered for use in drug/silicone adhesive matrix or laminate transdermal drug delivery systems.

EXAMPLE 22

Aging studies were carried out on laminates of DC 355 BIO PSA(R) with each enhancer. The effect of 1 wt % loading levels of cyclopentadecanone, Azone(R), ethanol, isopropyl myristate, isopropyl palmitate, and eucalyptol on initial tape properties of DC 355 machine coated laminates are shown in TABLE 14. The effect of these enhancers on tape properties of DC 355 after two weeks of aging are shown in TABLE 15. The tack, peel, and adhesion value for the control DC 355 laminates were reduced by 71, 509, and 5 percent, respectively from initial values (TABLE 14 vs. TABLE 15). Noted is that after two weeks of aging, only cyclopentadecanone increases the adhesion; while other decrease the adhesion (TABLE 15).

Examples 21 and 22 illustrate the tape properties resulted from the studies on the compatibility of cyclopentadecanone with silicone pressure sensitive adhesives. Cyclopentadecanone was found to increase the peel force, and reduce adhesion proportional to its loading level in both DC 355 and X7-2920 pressure sensitive adhesives. A maximum loading level of 10 wt % cyclopentadecanone was considered to be compatible with both DC 355 and x7-2920 BIO-PSA(R). Data obtained from a comparative study shows that the maximum compatible levels of other permeation enhancers with both 355 and x7-2920 BIO-PSA(R) were isopropyl palmitate (1 wt %), eucalyptol (<5 wt %). In conclusion, cyclopentadecanone can be incorporated into silicone pressure sensitive adhesives at higher levels than other enhancers and thus, can be considered for use in drug/silicone adhesive matrix or transdermal drug delivery systems.

TABLE 11

Effect of Skin Penetration Enhancers on Tape Properties of 355 Pressure Sensitive Adhesive

| Skin Enhancer | Loading Wt % | Initial Tape Properties[a] | | |
|---|---|---|---|---|
| | | Tack (g/cm$^2$) | Peel (g/cm) | Adhesion (g/cm) |
| Control | 0 | 92.0 | 1 +/− 0.2 | 290.0 |
| CIB-01 | 1 | 358.0 | 1.8 | 342.0 |
| (cyclopenta | 5 | 624.0 | 7.3 | 256.3 |
| decanone) | 10 | 780.7 | 9.1 | 193.7 |
| Ethanol[b] | 1 | 119.7 | 1.1 | 269.3 |
| | 5 | 239.0 | 1.4 | 263.0 |
| | 10 | 314.3 | 1.1 | 305.5 |
| Isopropyl | 1 | 407.3 | 3.5 | 506.6 |
| Palmitate | 5 | 864.0 | 9.1 | 172.6* |
| | 10 | 284.0 | 3.9 | 58.7** |
| Azone ® | 1 | 357.6 | 1.4 | 290.4 |
| | 5 | 212.7 | 2.5 | 322.7** |
| | 10 | 113.3 | 2.5 | 389.9** |

[a]Samples were hand-coated with a No. 8 coating bar. Severe compromise of tape properties (*), cohesive failure (**).
[b]Ethanol was very volatile and vaporized out during preparations. The final concentration of ethanol remaining in the patch was not able to be determined.

TABLE 12

Effect of Skin Penetration Enhancers on Tape Properties of X7-2920 Amine Resistant Pressure Sensitive Adhesive

| Skin Enhancer | Loading Wt % | Initial Tape Properties[a] | | |
|---|---|---|---|---|
| | | Tack (g/cm$^2$) | Peel (g/cm) | Adhesion (g/cm) |
| Control | 0 | 612.7 | 11.8 | 1170.0 |
| CIB-01 | 1 | 573.3 | 8.4 | 831.0 |
| (cyclopenta- | 5 | 598.0 | 11.6 | 2124.0 |
| decanone) | 10 | 915.3 | 15.5 | 2137.0 |
| Ethanol[b] | 1 | 246.3 | 3.5 | — |
| | 5 | 297.0 | 4.2 | 967.6 |
| | 10 | 288.3 | 5.6 | 960.1 |
| Isopropyl | 1 | 385.3 | 6.3 | 204.5 |
| Palmitate | 5 | 712.0 | 10.9 | 204.5 |
| | 10 | 524.7 | 14.1 | 290.7** |
| Azone ® | 1 | 312.0 | 1.8 | 1509.0 |
| | 5 | 703.0 | 16.9 | 1238.0** |
| | 10 | 714.3 | 22.9 | 1424.0** |

[a]Samples were hand-coated with a No. 8 coating bar. Severe compromise of tape properties, cohesive failure (**).
[b]Ethanol was very volatile and vaporized out during fabrication. The final concentration of ethanol remaining in the patch was not able to be determined.

TABLE 13

Effect of Skin Penetration Enhancers on Tape Properties of X7-2920 Amine Resistant Pressure Sensitive Adhesive

| Skin Enhancer | Loading Wt % | Initial Tape Properties[a] | | |
|---|---|---|---|---|
| | | Tack (g/cm$^2$) | Peel (g/cm) | Adhesion (g/cm) |
| Control | 0 | 115.0 | 0.7 +/− 0.9 | 720 +/− 38 |
| CIB-01 | 1 | 105.0 | 0.2 +/− 0.2 | 681 +/− 16 |
| (cylclopenta- | 5 | 403.0 | 7.0 +/− 1.4 | 623 +/− 29 |
| decanone) | 10 | 857.0 | 0.7 +/− 0.4 | 698 +/− 12 |
| Ethanol[b] | 1 | 84.0 | 1.0 +/− 0.4 | 697 +/− 10 |
| | 5 | 72.0 | 1.4 +/− 0.7 | 736 +/− 31 |
| | 10 | 60.0 | 18.9 +/− 1.1 | 477 +/− 50 |
| Isopropyl | 1 | 171.0 | 1.8 +/− 0.4 | 639 +/− 38 |
| Palmitate | 5 | 845.0 | 18.6 +/− 1.4 | 400 +/− 71 |
| | 10 | 758.0 | 17.2 +/− 2.8 | 445 +/− 91** |
| Azone ® | 1 | 758.0 | 1.4 +/− 0.4 | 716 +/− 46 |
| | 5 | 535.0 | 7.0 +/− 1.4 | 723 +/− 57 |

TABLE 13-continued

Effect of Skin Penetration Enhancers on Tape Properties of X7-2920 Amine Resistant Pressure Sensitive Adhesive

| Skin Enhancer | Loading Wt % | Initial Tape Properties[a] | | |
|---|---|---|---|---|
| | | Tack (g/cm²) | Peel (g/cm) | Adhesion (g/cm) |
| | 10 | 706.0 | 22.9 +/− 4.2 | 320 +/− 42** |

[a]Machine-coated samples. Severe compromise of tape properties, cohesive failure (**).
[b]Ethanol was very volatile and vaporized out during fabrication. The final concentration of ethanol remaining in the patch can not be determined.

TABLE 14

Compatibility of Skin Penetration Enhancers with DOW CORNING ® 355 Medical Grade Pressure Sensitive Silicone Adhesive

| Skin Enhancer | Loading Wt % | Initial Tape Properties, Mean +/− SD | | | | | |
|---|---|---|---|---|---|---|---|
| | | Tack (g/cm²) | %−[a] | Peel (g/cm) | %−[a] | Adhesion (g/cm) | %−[a] |
| Control | 0 | 187.0 | — | 1.4 +/− 0.0 | — | 466.1 +/− 17.9 | — |
| CIB-01[b] | 1 | 339.0 | +81 | 2.8 +/− 0.0 | +100 | 458.1 +/− 17.9 | −2 |
| Azone | 1 | 114.7 | −38 | 2.8 +/− 0.4 | +100 | 502.4 +/− 66.1 | +8 |
| Ethanol | 1 | 134.3 | −28 | 1.4 +/− 1.0 | +0 | 554.0 +/− 23.6 | +18 |
| Isopropyl Myristate | 1 | 295.3 | +58 | 7.4 +/− 0.7 | +21 | 486.2 +/− 27.8 | +4 |
| Isopropyl Palmitate | 1 | 229.3 | +22 | 6.3 +/− 0.7 | +350 | 536.8 +/− 32.0 | +15 |
| Eucalyptol | 1 | 158.7 | −15 | 1.4 +/− 1.1 | +0 | 465.4 +/− 23.6 | −2 |

[a]Percent change from control values for machine-coated laminates 1 mil thick.
[b]CIB-01 is cyclopentadecanone.

TABLE 15

Compatibility of Skin Penetration Enhancers with DOW CORNING ® 355 Medical Grade Pressure Sensitive Silicone Adhesive

| Skin Enhancer | Loading Wt % | Tape Properties, Mean +/− SD After Two Weeks Aging | | | | | |
|---|---|---|---|---|---|---|---|
| | | Tack | %−[a] | Peel | %−[a] | Adhesion | %−[a] |
| Control | 0 | 53.0 | −71 | 0.7 +/− 0.0 | −50 | 444.0 +/− 4.9 | −5 |
| CIB-01[b] | 1 | 103.0 | −70 | 1.4 +/− 0.3 | +50 | 515.7 +/− 32.6 | +13 |
| Azone | 1 | 90.0 | −22 | 1.8 +/− 0.4 | +36 | 483.0 +/− 19.3 | −4 |
| Ethanol | 1 | 48.7* | −63 | 2.1 +/− 0.4 | +50 | 525.6 +/− 3.2 | −5 |
| Isopropyl Myristate | 1 | 185.7 | −37 | 3.9 +/− 0.7 | −47 | 428.5 +/− 78.4 | −12 |
| Isopropyl Palmitate | 1 | 167.3 | −27 | 8.1 +/− | +30 | 414.1 +/− 60.8 | +23 |
| Eucalyptol | 1 | 41.0* | −74 | 0.4 +/− 0.7 | −71 | 416.6 +/− 95.9 | −10 |

[a]Percent change in the tape properties from initial for 1 mil thick machine-coated laminates. Severe compromise in tape properties. (*)
[b]CIC-01 is cyclopentadecanone.

Examples 23 to 26 illustrate other types of compositions which are also suitable. In these examples the amounts are given in percent by weight.

EXAMPLE 23

The following lotion formulation containing from about 0.001 to 1% by weight of estradiol may be prepared:

| | |
|---|---|
| Estradiol | 0.001-1 |
| Cetylalcohol | 15 |
| Propyleneglycol | 10 |
| Sodium lauryl sulfate | 15 |
| Cyclopentadecanone | 2 |
| Water q.s. | 100 |

EXAMPLE 24

The following cream formulation containing clotrimazole, and antifungal agent, may be prepared:

| | |
|---|---|
| Mineral oil | 31 |
| Cyclopentadecanone | 2 |
| Clotrimazole | 1 |
| Spermaceti | 10 |
| Glycerol monstearate | 10 |
| Paraffin | 8 |
| Water | |

EXAMPLE 25

The following suppository containing an antiseptic, benzethonium choloride, may be prepared:

| | |
|---|---|
| Benzethonium chloride | 2 |
| Cyclopentadecanone | 2 |
| Cocoa butter | 80 |
| Tween 61* | 16 |

*Polyethylene - 4 - sorbitan monostearate

EXAMPLE 26

The following film containing procaine hydrocholoride may be prepared:

| | |
|---|---|
| Procaine hydrocholoride | 0.562 |
| Cyclopentadecanone | 2 |
| Polyvinyl alcohol | 30 |
| Polyvinylpyrrolidone | 30 |
| Polyethylene glycol q.s. | 100 |

Following the above procedures but using those compounds where X is sulfur or imino of the structure

and when Y is oxygen, sulfur or imino of the structure =NR similar results of the enhancement of passage of drugs across body membranes were obtained. So we can conclude that these cyclic amides, cyclic amidines, cyclic thioesters, cyclic dithioesters and cyclic thioamides are effective as enhancers.

I claim:

1. A method for increasing the rate of passage of a drug across animal or human skin, mucous membranes, or the blood brain barrier which comprises applying to the skin, mucous membrane or blood brain barrier a composition comprising an effective amount of the drug, a pharmaceutical carrier, and from about 0.1 to about 50% by weight of a compound (with or without dissolving in a solvent) effecting such increase in rate, said compound having the structure:

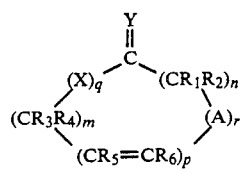

wherein X and Y are oxygen, sulfur or an imino group of the structure

or =N—R, with the proviso that when Y is an imino group, X is an imino group, and when Y is sulfur, X is sulfur or an imino group, A is a group having the structure

wherein X and Y are as defined above, m and n are integers having a value from 1 to 20 and the sum of m+n is not greater than 25, p is an integer having a value of 0 or 1, q is an integer having a value of 0 or 1, r is an integer having a value of 0 or 1, and each of R, $R_1$, $R_2$, $R_3$, $R_4$, $R_5$, and $R_6$ is independently hydrogen or an alkyl group having from 1 to 6 carbon atoms which may be straight chained or branched, provided that only one of $R_1$ to $R_6$ can be alkyl group, with the proviso that when p, q and r are 0 and Y is oxygen, then m+n is at least 11, and with the further proviso that when X is an imino group, q is equal to 1, Y is oxygen, and p and r are 0, then m+n is at least 11.

2. A method according to claim 1 wherein the amount of compound effecting the increase in the rate of passage is from about 0.1 to 30% by weight.

3. A method according to claim 1 wherein Y is sulfur, X is sulfur or imino, and A is

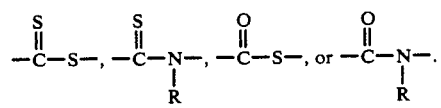

4. A method according to claim 1 wherein Y is imino, X is sulfur or imino, and A is

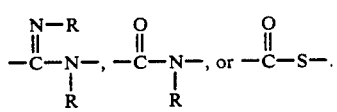

5. A method according to claim 1 wherein r is 0.

6. A method according to claim 5 wherein Y is sulfur and X is sulfur or imino.

7. A method according to claim 5 wherein Y is imino and X is imino.

8. A method according to claim 5 wherein Y is oxygen and X is sulfur or imino.

9. A method according to claim 1 wherein the R on the imino is lower alkyl.

10. A method according to claim 1 wherein the compound has the structure

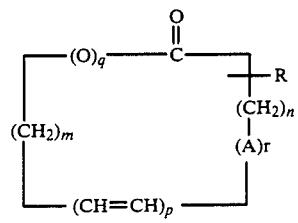

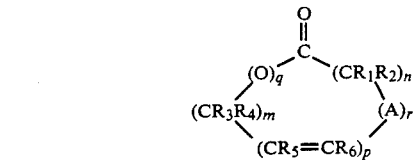

Wherein A is a carbo-oxy group of the structure

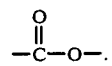

11. A method according to claim 10 wherein the amount of compound effecting the increase in the rate of passage is from about 0.1 to 30% by weight.

12. A method according to claim 10 wherein q and r are 1.

13. A method according to claim 12 wherein p is 0.

14. A method according to claim 13 wherein m+n is at least 3.

15. A method according to claim 10 wherein q is 1 and r is 0.

16. A method according to claim 15 wherein p is 0.

17. A method according to claim 10 wherein p, q and r are 0.

18. A method according to claim 17 wherein m+n is 11 to 15.

19. A method according to claim 18 wherein $R_1$, $R_2$, $R_3$, and $R_4$ are hydrogen.

20. A method according to claim 18 wherein one of $R_1$, $R_2$, $R_3$, or $R_4$ is lower alkyl.

21. A method according to claim 20 wherein one of $R_1$, $R_2$, $R_3$, or $R_4$ is methyl.

22. A method according to claim 19 wherein m+n is 11.

23. A method according to claim 19 wherein m+n is 14.

24. A method according to claim 21 wherein m+n is 14.

25. A method according to claim 10 wherein r is 0, q and p are 1, m is 7 and n is 7.

26. A method according to claim 10 wherein q is 1, and r are 0 and m+n is 15.

27. A method according to claim 17 wherein the concentration of the compound is at least 2%.

28. A composition for administering a drug across skin, mucous membranes or blood brain barrier which contains an effective amount of a drug, a pharmaceutical carrier, and from about 0.1% to about 50% by weight of a compound (with or without dissolving in a solvent) which increases the rate of passage of the drug across the skin, the mucous membranes, or the blood brain barrier, said compound having the structure:

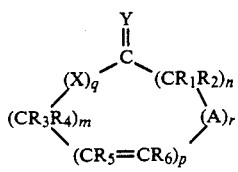

wherein X and Y are oxygen, sulfur or an imino group of the structure

or =N—R, with the proviso that when Y is an imino group, X is an imino group, and when Y is sulfur, X is sulfur or an imino group, A is a group having the structure

wherein X and Y are as defined above, m and n are integers having a value from 1 to 20 and the sum of m+n is not greater than 25, p is an integer having a value of 0 or 1, q is an integer having a value of 0 or 1, r is an integer having a value of 0 or 1, and each of R, $R_1$, $R_2$, $R_3$, $R_4$, $R_5$, and $R_6$ is independently hydrogen or an alkyl group having from 1 to 6 carbon atoms which may be straight chained or branched, provided that only one of $R_1$ to $R_6$ can be alkyl group, with the proviso that when p, q and r are 0 and Y is oxygen, then m+n is at least 11, and with the further proviso that when X is an imino group, q is equal to 1, Y is oxygen, and p and r are 0, then m+n is at least 11.

29. A composition according to claim 28 wherein each of X and Y is oxygen and wherein A is a carbo-oxy group of the structure

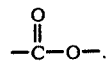

30. A composition according to claim 29 wherein q and r are 1.

31. A composition according to claim 30 wherein p is 0.

32. A composition according to claim 30 wherein m+n is at least 3.

33. A composition according to claim 29 wherein q is 1 and r is 0.

34. A composition according to claim 33 wherein p is 0.

35. A composition according to claim 29 wherein p, q and r are 0.

36. A composition according to claim 35 wherein m+n is 11 to 15.

37. A composition according to claim 36 wherein $R_1$, $R_2$, $R_3$, and $R_4$ are hydrogen.

38. A composition according to claim 36 wherein one of $R_1$, $R_2$, $R_3$, or $R_4$ is lower alkyl.

39. A composition according to claim 38 wherein one of $R_1$, $R_2$, $R_3$, or $R_4$ is methyl.

40. A composition according to claim 37 wherein m+n is 11.

41. A composition according to claim 37 wherein m+n is 14.

42. A composition according to claim 39 wherein m+n is 14.

43. A composition according to claim 29 wherein r is 0, p and q are 1, m is 7 and n is 7.

44. A composition according to claim 29 wherein q is 1, p and r are 0, and m+n is 15.

45. A composition according to claim 35 wherein the concentration of the compound is at least 2%.

46. A composition according to claim 44 wherein the concentration of the compound is at least 0.5%.

47. A composition according to claim 29 which is the form of a lotion.

48. A composition according to claim 29 which is the form of a cream.

49. A composition according to claim 29 which is the form of a film.

50. A composition according to claim 29 which is the form of a dermal patch.

51. A composition according to claim 29 which is the form of a solution.

52. A composition according to claim 29 which is the form of a spray solution.

53. A composition according to claim 51 wherein the composition is held in a sponge.

* * * * *